US012582784B2

(12) United States Patent
Smutney et al.

(10) Patent No.: US 12,582,784 B2
(45) Date of Patent: Mar. 24, 2026

(54) DRY POWDER INHALATION SYSTEM

(71) Applicant: MannKind Corporation, Danbury, CT (US)

(72) Inventors: Chad C. Smutney, Watertown, CT (US); P. Spencer Kinsey, Sandy Hook, CT (US); John M. Polidoro, Tolland, CT (US); Carl R. Sahi, Coventry, CT (US); Benoit Adamo, South Salem, NY (US); Scott McLean, Sandy Hook, CT (US); Dennis Overfield, Lyme, CT (US); Anthony Bryant, Stratford, CT (US)

(73) Assignee: Mannkind Corporation, Danbury, CT (US)

( * ) Notice: Subject to any disclaimer, the term of this patent is extended or adjusted under 35 U.S.C. 154(b) by 445 days.

(21) Appl. No.: 18/099,829

(22) Filed: Jan. 20, 2023

(65) Prior Publication Data

US 2023/0149641 A1 May 18, 2023

Related U.S. Application Data

(63) Continuation of application No. 16/718,732, filed on Dec. 18, 2019, now abandoned, which is a continuation of application No. 14/863,136, filed on Sep. 23, 2015, now abandoned, which is a continuation of application No. 12/413,405, filed on Mar. 27, 2009, now abandoned.

(60) Provisional application No. 61/143,370, filed on Jan. 8, 2009, provisional application No. 61/040,112, filed on Mar. 27, 2008.

(51) Int. Cl.
*A61M 15/00* (2006.01)
*A61M 16/00* (2006.01)

(52) U.S. Cl.
CPC .... *A61M 15/0023* (2014.02); *A61M 15/0015* (2014.02); *A61M 15/002* (2014.02); *A61M 15/0028* (2013.01); *A61M 15/0043* (2014.02); *A61M 2016/0021* (2013.01); *A61M 2016/0027* (2013.01); *A61M 2202/064* (2013.01); *A61M 2202/07* (2013.01); *A61M 2205/58* (2013.01); *A61M 2205/581* (2013.01); *A61M 2205/582* (2013.01)

(58) Field of Classification Search
CPC ............ A61M 15/002; A61M 15/0028; A61M 2202/064
See application file for complete search history.

(56) References Cited

U.S. PATENT DOCUMENTS

2004/0182387 A1* 9/2004 Steiner .............. A61M 15/0028 128/203.15
2009/0050142 A1* 2/2009 Hamano ............... A61M 15/02 128/200.23
2009/0110647 A1* 4/2009 Richardson ............ A61K 45/06 514/4.8

FOREIGN PATENT DOCUMENTS

EP 1923087 A2 * 5/2008 ........ A61M 15/0028
WO WO-2007068896 A1 * 6/2007 .......... A61M 16/127

OTHER PUBLICATIONS

De Koning, J.P. et al. "Effect of an external resistance to airflow on the inspiratory flow curve" International Journal of Pharmaceutics 234 (2002) 257-266 (Year: 2002).*

* cited by examiner

*Primary Examiner* — Andrew S Rosenthal
(74) *Attorney, Agent, or Firm* — K&L Gates LLP; Brian J. Novak; David W. Old

(57) ABSTRACT

Dry powder inhaler systems for pulmonary delivery of pharmaceuticals are disclosed.

17 Claims, 22 Drawing Sheets

DRY POWDER INHALATION SYSTEM

CROSS REFERENCE TO RELATED APPLICATIONS

This application is a continuation of patent application Ser. No. 16/718,732 filed Dec. 18, 2019, which is a continuation of patent application Ser. No. 14/863,136 filed Sep. 23, 2015, which is a continuation of patent application Ser. No. 12/413,405 filed Mar. 27, 2009, which claims the benefit under 35 U.S.C. § 119 (e) of United States Provisional Application Ser. Nos. 61/040,112 filed Mar. 27, 2008 and 61/143,370 filed Jan. 8, 2009; the contents of each of these applications are incorporated by reference herein in their entirety.

TECHNICAL FIELD

A pulmonary drug delivery system is disclosed. The system includes a dry powder inhaler; and a unit dose cartridge for using with the inhaler. The cartridge can contain a drug delivery formulation for pulmonary delivery, for example, a formulation comprising a diketopiperazine and an active ingredient including peptides and proteins such as insulin and glucagon-like peptide 1. The dry powder inhaler is compact and comprises a housing, and a mouthpiece having a chamber to install the unit dose cartridge containing medicament and can be separated from its housing for ease of cleaning.

All references cited in this specification, and their references, are incorporated by reference herein in their entirety where appropriate for teachings of additional or alternative details, features, and/or technical background.

BACKGROUND

Drug delivery systems for the treatment of disease which introduce active ingredients into the circulation are numerous and include oral, transdermal, inhalation, subcutaneous and intravenous administration. Drugs delivered by inhalation are typically delivered using positive pressure relative to atmospheric pressure in air with propellants. Such drug delivery systems deliver drugs as aerosols, nebulized or vaporized. More recently, drug delivery to lung tissue has been achieved with dry powder inhalers. Dry powder inhalers can be breath-activated to deliver drugs by converting drug particles in a carrier into a fine dry powder which is entrained into an airflow and inhaled by the patient. Drugs delivered with the use of a dry powder inhaler can no longer be intended to treat pulmonary disease only, but also specific drugs can be used to treat many conditions, including diabetes and obesity.

Dry powder inhalers, used to deliver medicaments to the lungs, contain a dose system of a powder formulation usually either in bulk supply or quantified into individual doses stored in unit dose compartments, like hard gelatin capsules or blister packs. Bulk containers are equipped with a measuring system operated by the patient in order to isolate a single dose from the powder immediately before inhalation. Dosing reproducibility requires that the drug formulation is uniform and that the dose can be delivered to the patient with consistent and reproducible results. Therefore, the dosing system must operate to completely discharge all of the formulation effectively during an inspiratory maneuver when the patient is taking his/her dose. Flow properties of the powder formulation, and long term physical and mechanical stability in this respect, are more critical for bulk containers than they are for single unit dose compartments. Good moisture protection can be achieved more easily for unit dose compartments such as blisters, however, foils used to seal the blisters and subsequent drug formulation lose viability with long storage.

Dry powder inhalers such as those describe in U.S. Pat. No. 7,305,986 and U.S. patent application Ser. No. 10/655,153 (US 20040182387), the disclosures of which are incorporated herein by reference in their entirety for all they disclose regarding dry powder inhalers, can generate primary drug particles or suitable inhalation plumes during an inspiratory maneuver by deagglomerating the powder formulation within a capsule. The amount of fine drug discharged from the inhaler's mouthpiece during inhalation is largely dependent on the interparticulate forces in the powder formulation (between drug and drug particles or between drug and excipient particles) and the efficiency of the airflow as measured by pressure drop and flow rate entering and exiting the dry powder dispenser. The benefits of delivering drugs via the pulmonary circulation are numerous and include, rapid absorption into the arterial circulation, avoidance of drug degradation by liver metabolism, ease of use, i.e., lack of discomfort of administration by other routes of administration.

Dry powder inhaler products developed for pulmonary inhalation have met with limited success to date, due to lack of practicality. Some of the persistent problems observed with prior art inhalers, include ruggedness of device, inconsistency in dosing, inconvenience of the equipment, and/or lack of patient compliance. Therefore, the inventors have designed and manufactured a dry powder inhaler with consistent drug delivery properties, ease of use without discomfort, improved ruggedness, and discrete geometries which would allow for better patient compliance.

SUMMARY

Dry powder inhaler systems for pulmonary delivery of pharmaceuticals are disclosed. The dry powder inhalation systems comprise a dry powder inhalation device or inhaler and at least one cartridge containing a pharmaceutical formulation comprising at least one active ingredient for delivery to the pulmonary circulation. The present inhalation systems provide rugged devices which are reusable, use pre-metered unit dose cartridges and can be separated into their principal component parts for ease of cleaning. The devices also provide high resistance inhalation systems which enable deagglomeration of dry powder particles, have consistent airflow and are simple and easy to use.

In one embodiment, a dry powder inhaler comprises a housing, and a mouthpiece, wherein the housing comprises a mouthpiece engaging section structurally configured to engage with the mouthpiece, and the mouthpiece being removable at predetermined positions relative to the housing, and having a conduit permitting airflow between an air inlet and an air exit port, and comprising a chamber and an oral placement section; the mouthpiece further being structurally configured to be moveable within the housing in an engaged position and releasable from the housing at a predetermined position. The dry powder inhaler mouthpiece is structurally configured to receive, hold and/or release a medicament containing cartridge in the chamber.

In another embodiment, the housing comprises a container structurally configured to adapt to the mouthpiece and has one or more openings for allowing air intake into the mouthpiece chamber. In such an embodiment, the housing has securing mechanisms to hold the mouthpiece chamber and permit the mouthpiece assembly to be moveable within the housing to a storage position, to a cartridge loading/unloading position, mouthpiece separable position, to an inhalation position and in reversed order.

In still another embodiment, the mouthpiece assembly engages the mouthpiece at the mouthpiece engaging section of the housing. The housing can comprise an air intake section having an air conduit with one or more first openings to allow ambient air intake and a second opening in communication with the mouthpiece engaging section which allows airflow through the air conduit and out into the housing engaging section, the engagement of the mouthpiece substantially prevents ambient air from entering the conduit except at the one or more first openings in the housing for air intake. In one embodiment, the housing also comprises a mouthpiece storage section.

In yet another embodiment, the dry powder inhaler mouthpiece assembly can move relative to the housing and the movement of the mouthpiece within the housing can reconfigure a cartridge seated in the inhaler from a closed configuration to an open configuration, or from an open to a closed configuration. Movement of the mouthpiece within the housing can be of various types, such as translational or rotational. In one such embodiment, movement about the housing is rotational, and can be restricted at predetermined locations relative to the housing to provide registration of positions of the mouthpiece in use. In one embodiment, for example, movement of the mouthpiece assembly is rotational and the mouthpiece can rotate from the storage position to a cartridge loading/unloading position to an inhalation position. In another embodiment, the mouthpiece further comprises a mouthpiece oral placement section and a medicament containing cartridge receiving section; the cartridge receiving section configured to permit and direct air flow through and around the cartridge.

In a further embodiment, the air conduit of the air intake section of the housing is in communication with the air exit port of the mouthpiece when the cartridge is in an open configuration. The airflow conduit is established between one or more first openings in the housing; then air passes through the airflow conduit within the housing and exits a second opening of the mouthpiece engaging section and enters into the mouthpiece chamber wherein a percentage of intake air volume goes through the cartridge and a percentage of intake air volume goes around the cartridge during an inhalation maneuver. In this embodiment, the airflow path then enters the mouthpiece chamber and enters and exits the conduit of the mouthpiece oral placement section. In a further embodiment, with a cartridge containing medicament placed in the chamber, airflow entering the chamber from the housing outlet port is diverted so that a percentage of the airflow volume goes through the cartridge and a percentage of the airflow volume goes around the cartridge. Both air flow volumes, exiting the cartridge with a medicament and airflow around the cartridge, converge prior to entering and exiting the air exit port of the mouthpiece of the oral placement section.

In another embodiment, a dry powder inhaler is provided comprising a housing, and a mouthpiece assembly, the housing having a top wall, a bottom wall, side walls; a mouthpiece engaging section, a mouthpiece storage section, and an air intake section having a conduit with a first opening to allow ambient air intake and a second opening in communication with the mouthpiece engaging section which allows air flow therethrough; the mouthpiece subassembly being removable and comprising a chamber structurally configured to house a cartridge and to engage with the mouthpiece engaging section of the housing; an oral placement section extending from the chamber and having an air inlet which communicates with the chamber and an air outlet in communication with ambient air.

In embodiments described herewith, a breath-powered inhaler is provided comprising, an inhaler with resistance values that can be tunable or changed as required by the patient being an adult or a child. In one embodiment, the resistance values of the inhaler can be altered by changing the geometries or configuration of the air conduits so that airflow distribution through the cartridge and around the cartridge can vary. In one embodiment, inhaler resistance values can range between 0.08 and 0.15 √kPa/liters per minute. In certain embodiments, flow balance distribution can range from about 10% to about 30% through the cartridge and from about 70% to 90% going around the cartridge.

In still a further embodiment, the dry powder inhalation system comprises a breath-activated dry powder inhaler, a cartridge containing medicament, wherein the medicament can comprise a diketopiperazine and an active agent. In some embodiments, the active agent comprises peptides and proteins. In another embodiment, the inhalation system comprises a cartridge containing medicament wherein the peptide or protein can be an endocrine hormone: including, insulin, glucose-like peptide (GLP-1), parathyroid hormone, parathyroid hormone related protein (PTHrP), and the like.

In one embodiment, the dry powder inhalation system can comprise a cartridge including a formulation for pulmonary delivery which can be provided for use with different dosage strengths, wherein the system can deliver the dosage with consistency and in a linear manner. In this embodiment, for example, multiple cartridges of a single dose to be administered to a subject can be interchangeably replaced or substituted by providing the system with a single cartridge of the sum of the dosage strength of the multiple cartridges, wherein the system can deliver a bioequivalent dose with a single cartridge.

BRIEF DESCRIPTION OF THE DRAWINGS

FIG. 11 also depicts a cartridge embodiment for use with a dry powder inhaler according to the present description.

DETAILED DESCRIPTION

In embodiments disclosed herein, there are disclosed dry powder inhalation systems for delivering pharmaceutical medicaments to the pulmonary circulation. The inhalation systems comprise a breath-powered or breath activated, dry powder inhaler, one or more cartridges containing a pharmaceutical formulation comprising one or more pharmaceutically active substances or active ingredients, and a pharmaceutically acceptable carrier.

Figure 1:
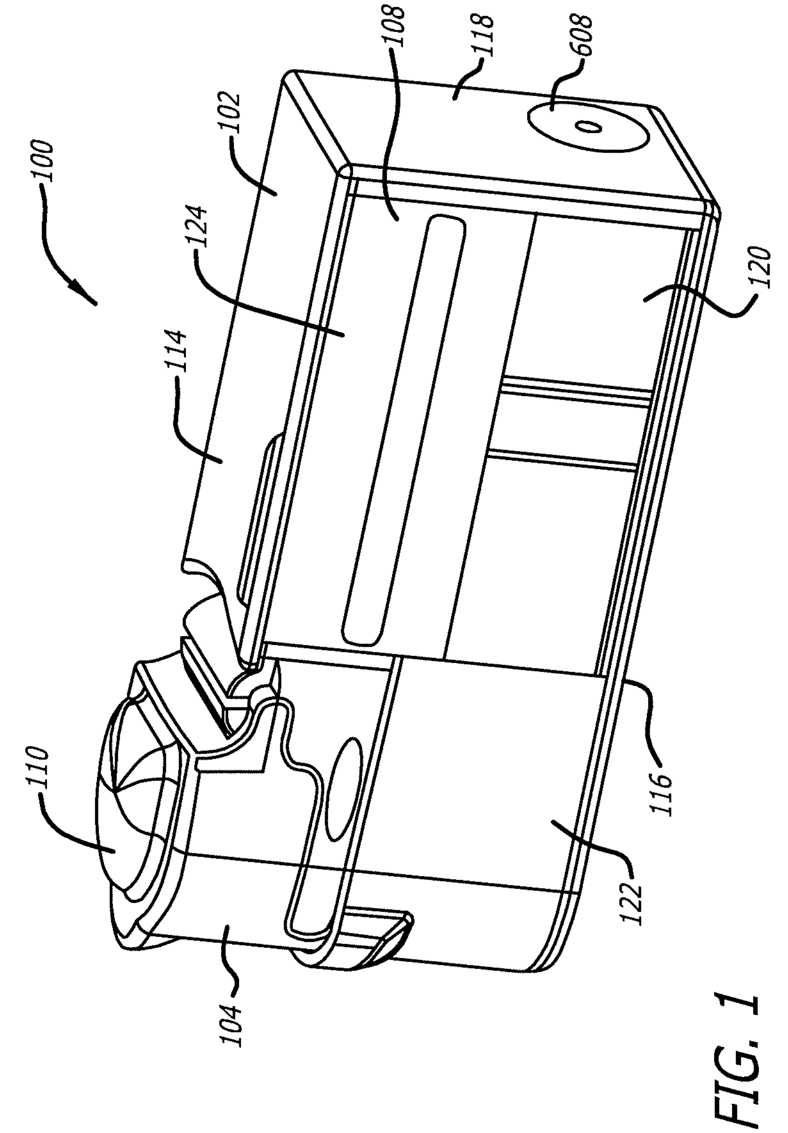
FIG. 1 illustrates a three dimensional side view of an embodiment of a dry powder inhaler in a storage position.

One embodiment of a dry powder inhaler is shown in FIG. 1. Therein, dry powder inhaler 100 comprises housing 102, and removable mouthpiece assembly or subassembly 104. FIG. 1 illustrates dry powder inhaler 100 in a closed or storage position, wherein mouthpiece oral placement section 106 (illustrated in FIG. 2) is stowed away under cover 108. FIG. 1 also illustrates cover or lid 110 over mouthpiece chamber 112 (illustrated in FIG. 2). In one embodiment of FIG. 1, housing 102 is structurally configured to be relatively rectangular in shape and has top wall 114, bottom wall 116, back wall 118, first side wall 120, second side wall (not illustrated), mouthpiece engaging section 122, mouthpiece storage section 124, and an air intake section as part of housing 102.

Figure 2:
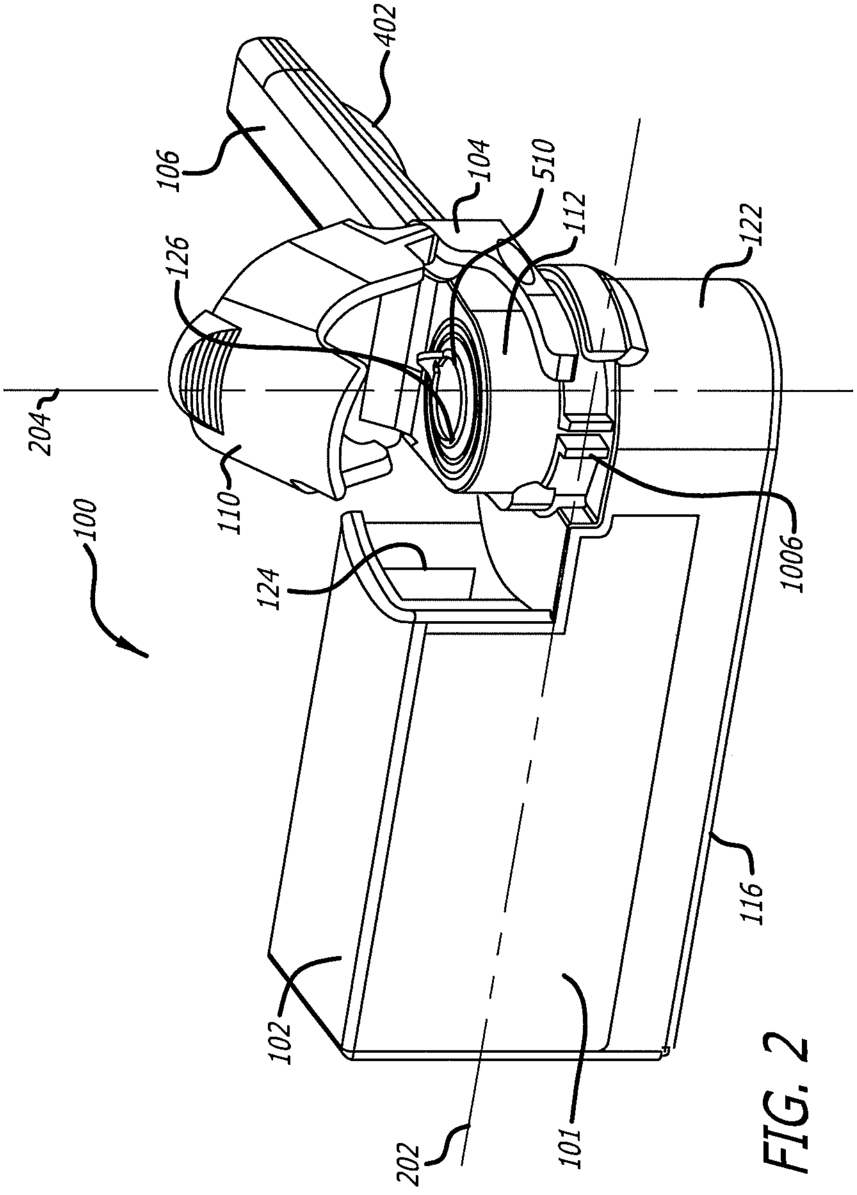
FIG. 2 illustrates the back side view of the dry powder inhaler of FIG. 1 showing the mouthpiece subassembly moved from the storage position to a cartridge loading position wherein the cap is opened. In this embodiment, this is also the position at which the mouthpiece can be separated.

FIG. 2 illustrates dry powder inhaler 100 from FIG. 1, showing the inhaler in a cartridge loading/unloading position with lid 110 open to allow a mating cartridge to be inserted into the central cavity of mouthpiece chamber 112. FIG. 2 also illustrates removable mouthpiece subassembly 104 is movable from the storage position in the housing to about 90° relative to longitudinal x-axis 202 of housing 102 rotated about y-axis 204. In certain embodiments, the cartridge loading/unloading position of mouthpiece assembly 104 can be any predetermined angle as desired. As illustrated in FIG. 2, mouthpiece engaging section 122 of housing 102 is relatively circular in shape on the side wall and is shorter in height compared to the rest of housing 102 to accommodate mouthpiece chamber 112 and can form one end of inhaler 100. Housing 102 can also comprise an air conduit with one or more first openings to allow ambient air intake and a second opening in communication with mouthpiece engaging section 122 which allows air flow from the intake section through the conduit into mouthpiece chamber 112 in the inhalation position.

Figure 3:
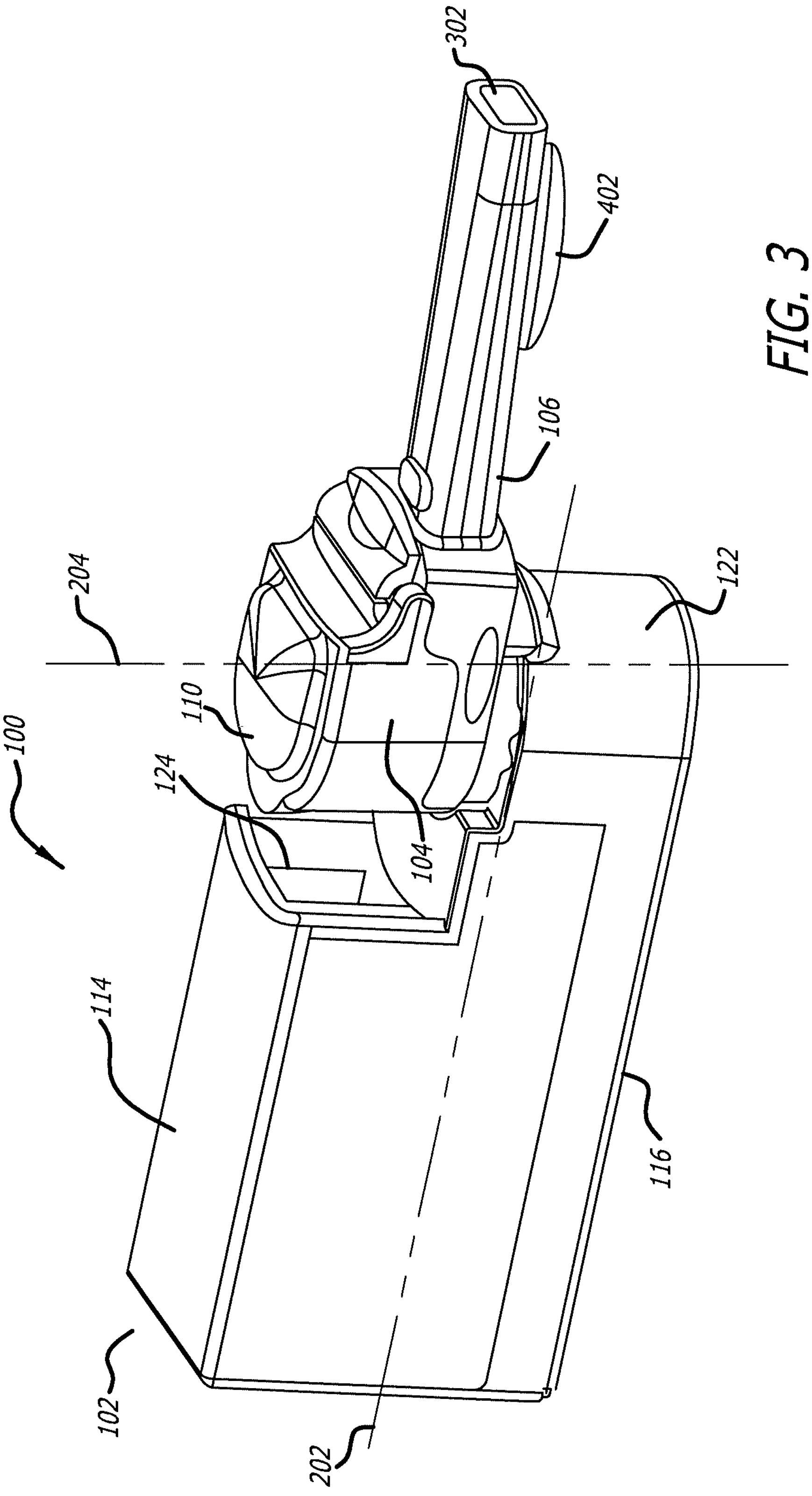
FIG. 3 illustrates the back side view of the dry powder inhaler of FIG. 1 showing the mouthpiece subassembly has been moved to the inhalation position for use.

FIG. 3 depicts dry powder inhaler 100 illustrated in FIG. 1, showing removable mouthpiece assembly 104 in an extended or inhalation position. In this embodiment, removable mouthpiece assembly 104 is at about 180° angle relative to the longitudinal x-axis 202 of housing 102 rotated about y-axis 204. In some embodiments, the inhalation position of mouthpiece assembly 104 can be varied depending on the structural configuration of the cartridge design to be adapted with the inhaler, and the rotational degrees a cartridge may be rotated to properly align apertures that allow air to enter and exit the cartridge carrying a plume of medicament into mouthpiece exit port 302.

Figure 4:
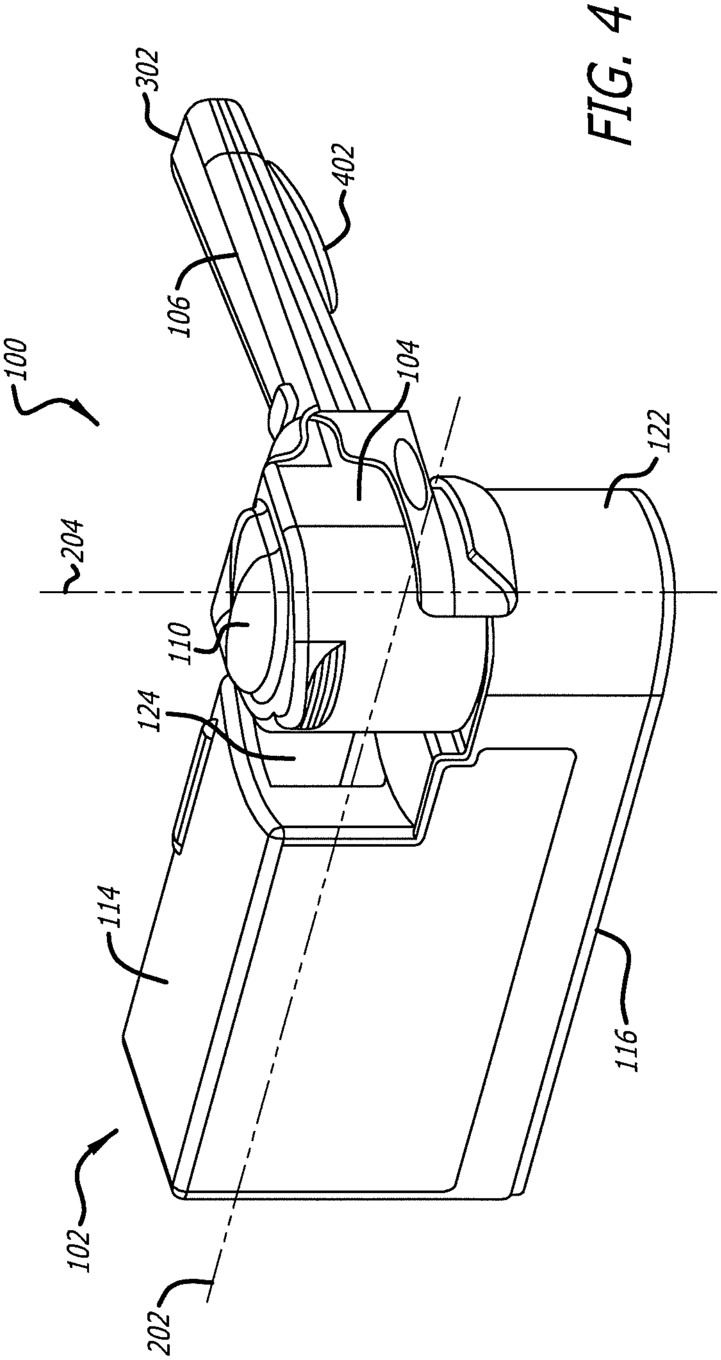
FIG. 4 illustrates the back side view of the dry powder inhaler of FIG. 1 showing the mouthpiece subassembly has been moved to an unloading position after inhalation.

FIG. 4 illustrates dry powder inhaler 100 of FIG. 1 showing removable mouthpiece assembly 104 being moveable about the loading/unloading position after use. It should be noted that lid 110 remains closed during movement of removable mouthpiece assembly 104 about housing 102. FIG. 4 also illustrates mouthpiece oral placement section 106 can be configured with tongue depressor 402 which acts to properly depress the tongue of a user.

Figure 5:
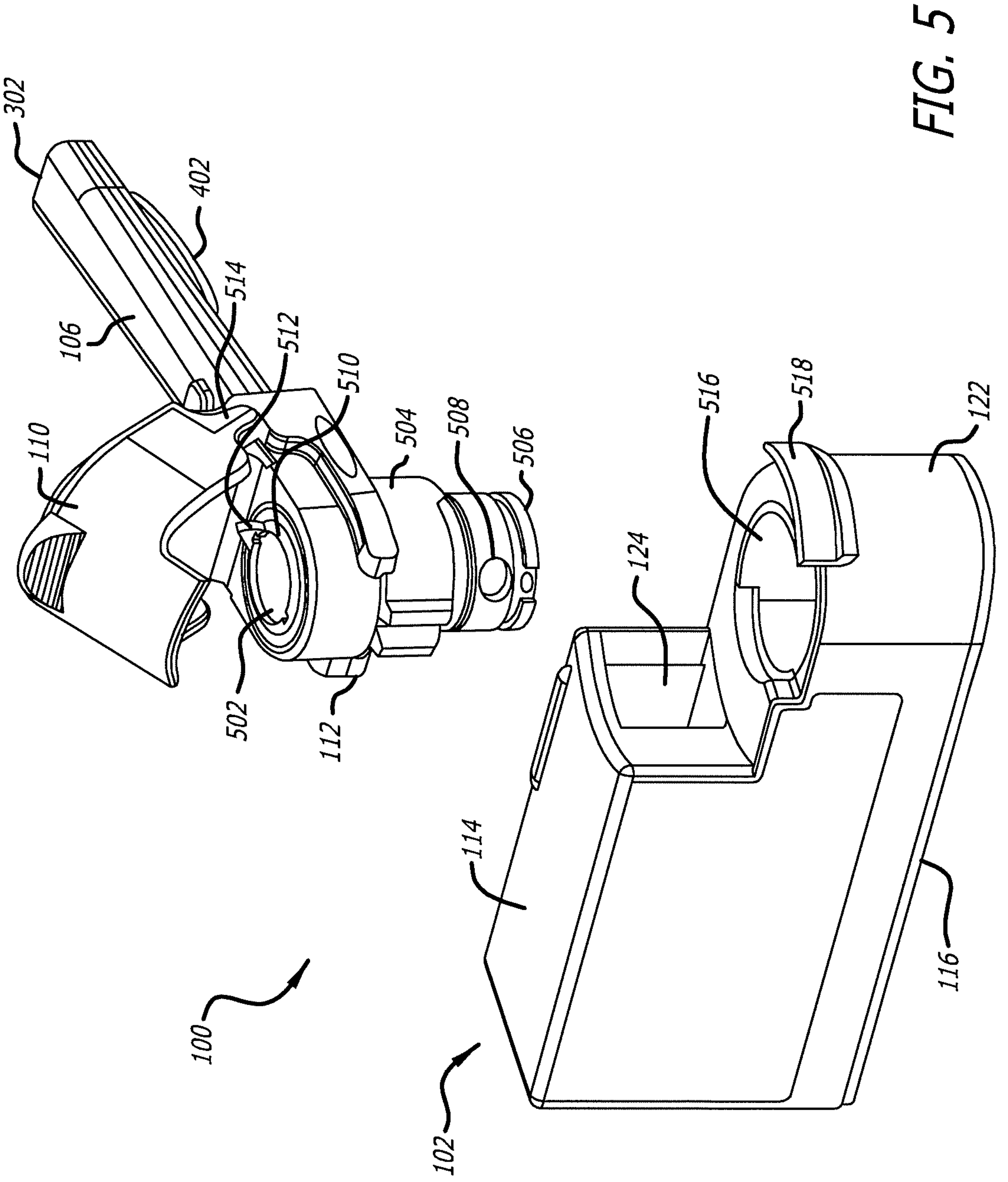
FIG. 5 illustrates the dry powder inhaler of FIG. 1, showing the housing subassembly and the mouthpiece subassembly disengaged from one another.

FIG. 5 illustrates dry powder inhaler 100 of FIG. 1 comprising the component parts, removable mouthpiece assembly 104 and housing 102. Removable mouthpiece assembly 104 comprising mouthpiece chamber 112 structurally configured with cartridge holder area 502, one or more belts 504 and one or more flanges 506, lid 110 and air inlet port 508 which communicates with the housing second opening to engage with mouthpiece engaging section 122 of housing 102; mouthpiece oral placement section 106 extending from mouthpiece chamber 112 and having air inlet port 508 which communicates with mouthpiece chamber 112 and mouthpiece exit port 302 which is in communication with ambient air. Drive key 510 structurally configured to have indicator 512, for example, in the shape of a tear drop for proper placement of a cartridge in dry powder inhaler 100 is also shown in FIG. 2 and FIG. 5. Proper alignment of a cartridge in the inhaler indicates the correct relative rotational orientation and determines successful cartridge seating, insertion and emptying in use. In such an embodiment, a cartridge cannot be properly seated unless tear drop 1602 of cartridge 1600 (FIG. 11) and drive key 510 align with one another.

Lid 110 is positioned over mouthpiece chamber 112 and is mechanically connected to removable mouthpiece assembly 104 by hinge 514. Lid 110 has an outer surface and an inner surface and it is structurally configured with an anvil in its inner top surface and relatively centered within the top. Lid 110 can only be opened when removable mouthpiece assembly 104 is in the loading/unloading position. When removable mouthpiece assembly 104 is engaged into housing 102 an interlocking mechanism prevents movement to a dosing/inhalation position or to a storage position when lid 110 is opened or raised. The interlocking mechanism can comprise, for example, one or more belts or flexible radial arms, which are incorporated into the walls of mouthpiece chamber 112 and act as a self-synching mechanism 602 in FIG. 6. The interlocking mechanism allows removable mouthpiece assembly 104 to obtain proper registration of the various positions when dry powder inhaler 100 is in use. Lid 110 can be maintained in a closed position by a locking mechanism, for example, a spring loaded boss such as a lock-out button which can engage a receiving detent within housing 102. In an alternate embodiment, the locking mechanism comprises an upward extension of the housing wall. The locking mechanism 602 can also serve to secure the mouthpiece subassembly against further rotation. Position registration of removable mouthpiece assembly 104 allows the inhaler to be properly used and prevents movement of removable mouthpiece assembly 104 to the dosing position without lid 110 being depressed.

FIG. 5 also illustrates housing 102 separated from removable mouthpiece assembly 104 showing mouthpiece engaging section 122 having an opening or cavity 516 with top wall 114 partially discontinuous to adapt, receive and hold removable mouthpiece assembly 104 and structurally configured to accommodate the mouthpiece. Housing 102 is configured to have an upward projection of the wall or second flange 518 around the top outer portion of mouthpiece engaging section 122 and a protrusion configured as a drive key in its bottom wall configured to mate with a keying structure of a cartridge. The proper alignment of a cartridge within dry powder inhaler 100 is dependent on drive key 510 having an indicator 512 and one or more indentation 126 (FIG. 2) in removable mouthpiece assembly 104 and drive key 510 and of housing 102.

Figure 6:
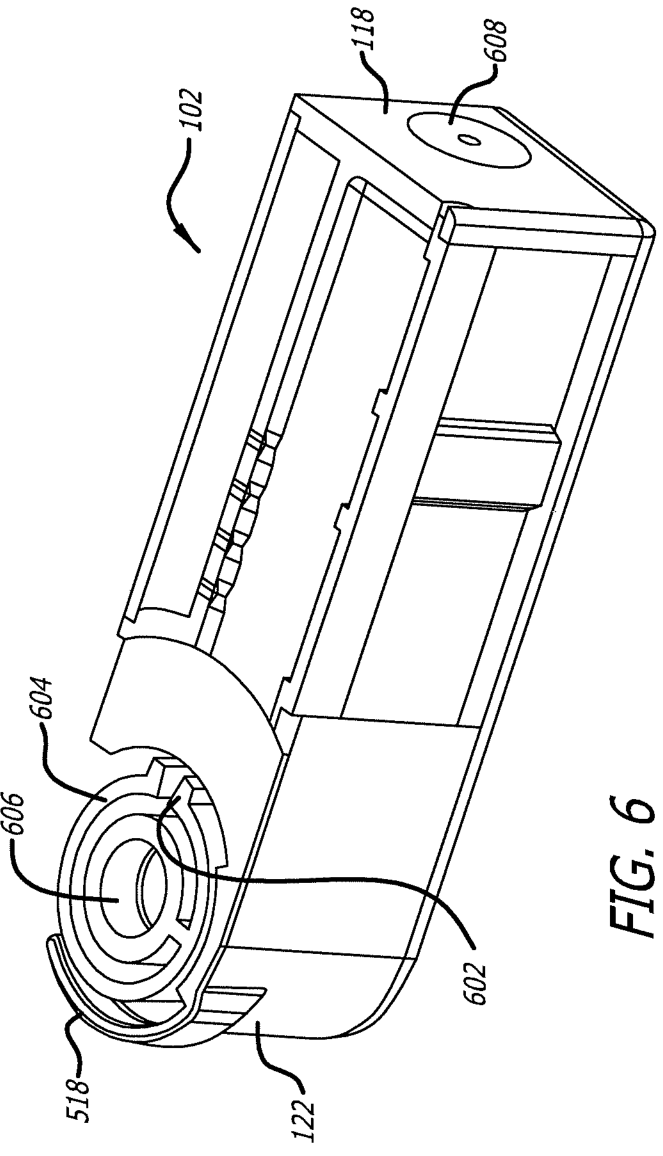
FIG. 6 illustrates a top view section of a housing subassembly of a dry powder inhaler.

Housing 102 comprises mouthpiece engaging section 122 having an outer wall, an inner wall and a bottom wall contiguous with the side and bottom walls respective of housing 102, and configured to adapt to the mixing section of removable mouthpiece assembly 104. FIG. 6 illustrates a parallel cross-section through the mid-longitudinal plane of housing 102 containing a portion of mouthpiece chamber 112. FIG. 6 also illustrates interlocking mechanism 604 (belts 504 in FIG. 5); chamber inner wall 606 defining a space for housing a cartridge. Circular structure or plug 608 is the wall of the air conduit of housing 102 which is continuous with back wall 118 of housing 102.

Figure 7:
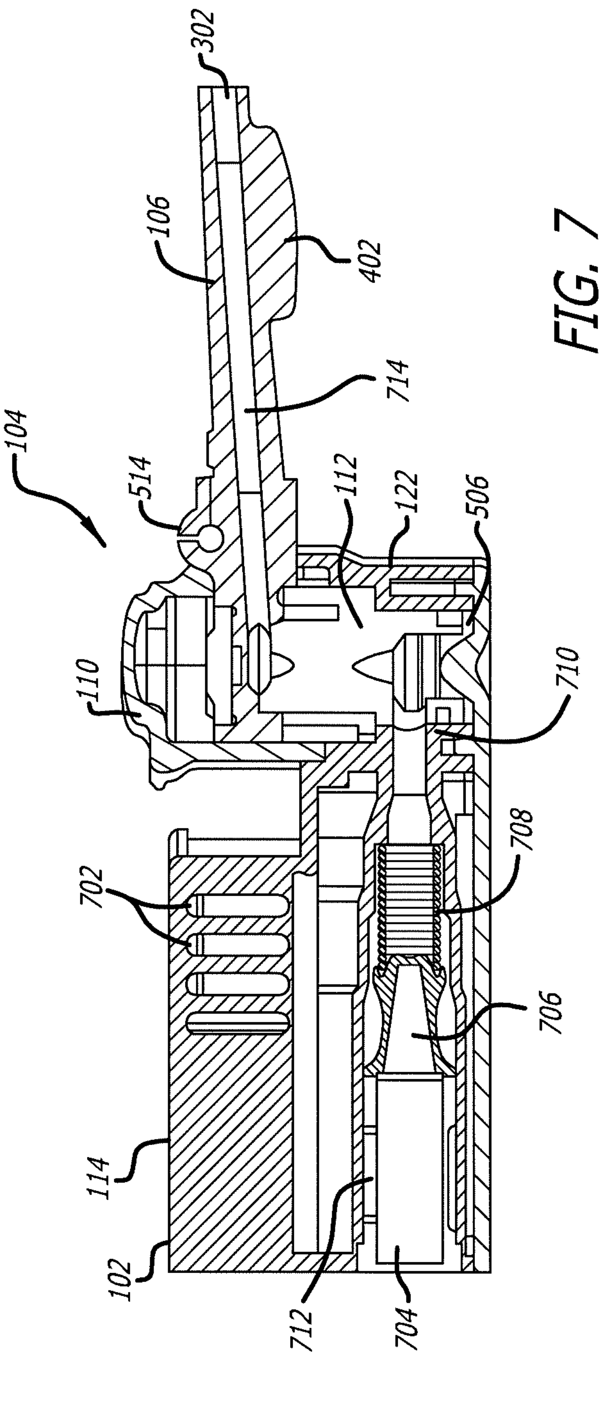
FIG. 7 illustrates the dry powder inhaler shown in FIG. 3 in cross-section.

FIG. 7 illustrates a cross sectional view of dry powder inhaler 100 in a dosing or inhalation position. As seen in FIG. 7, housing 102 has a substantially rectangular shape, however other shapes are also suitable. Housing 102 comprises one or more inlet ports or first openings 702, air conduit 704, housing piston 706 and spring 708, and outlet port 710 opening into mouthpiece engaging section 122 and aligns with the inlet port of mouthpiece chamber 112. Air conduit 704 has one or more openings 712 that allow airflow to enter.

Figure 8:
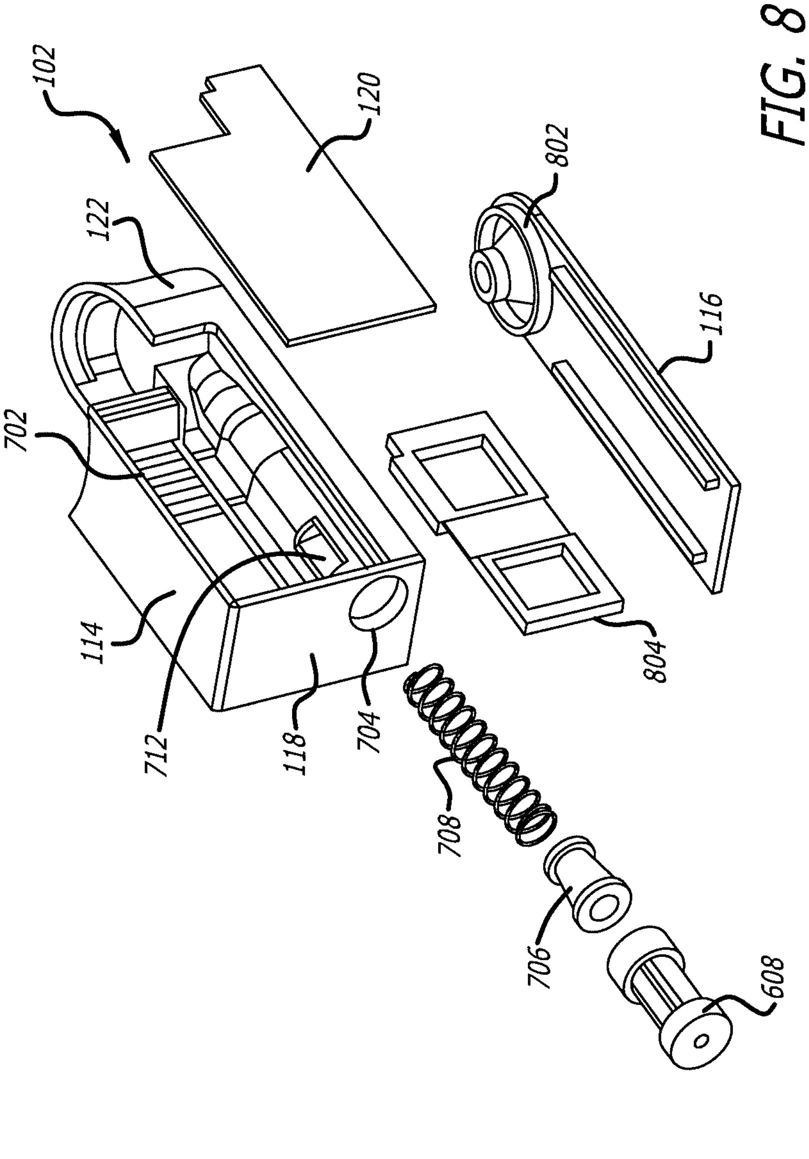
FIG. 8 illustrates the dry powder inhaler of FIG. 1, showing an exploded view of the housing subassembly.

Mouthpiece engaging section 122 is partially configured in the shape of a cup further comprising second drive key 802 as seen in FIG. 8 from bottom wall 116 configured to receive and hold a medicament containing cartridge. FIG. 7 also shows the engagement between flange 506 of mouthpiece chamber 112 in housing 102; hinge 514, lid 110 and mouthpiece oral placement section 106 with tongue depressor 402 and airflow conduit 714 of removable mouthpiece assembly 104.

Figure 9:
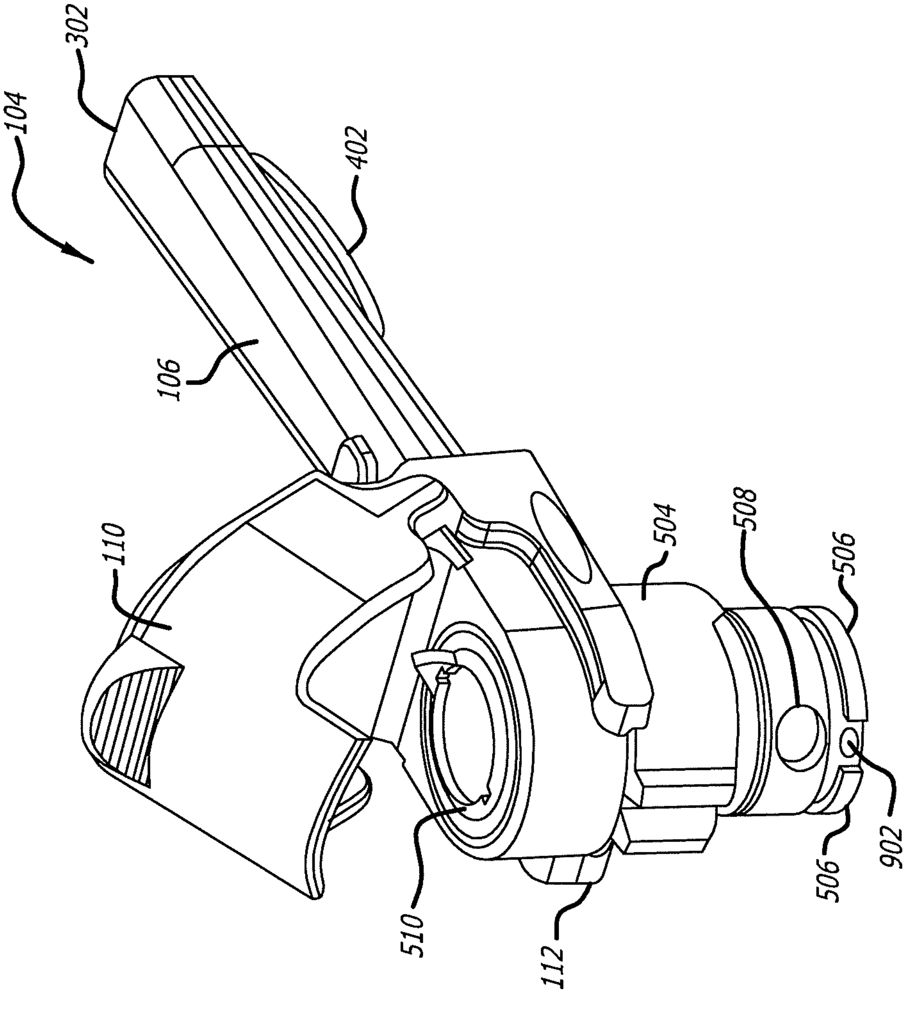
FIG. 9 illustrates the dry powder inhaler of FIG. 1, showing the mouthpiece subassembly removed from the housing component.

FIG. 8 depicts an exploded view of housing 102 illustrating integral components of dry powder inhaler 100, including plug 608, piston 706 and spring 708 which assemble into air conduit 704; housing 102 outer structure comprising back wall 118, side wall 120, top wall 114, and bottom wall 116; mouthpiece engaging section 122 with second drive key 802, and slide door 804 which covers the storage compartment for mouthpiece oral placement section 106. Air conduit 704 is configured to have an aperture or opening 712 which allows and directs airflow entering housing 102 into mouthpiece engaging section 122 during an inspiratory maneuver. Mouthpiece engaging section 122 can also comprise a securing mechanism which can comprise protrusions or projections from the inner wall of the chamber which mates with flange 506 and mating structure 902 as seen in FIG. 9 of mouthpiece chamber 112. In this embodiment, piston 706 and compression spring 708 act as an indicator mechanism positioned in air conduit 704 of housing 102 structurally configured to indicate inspiratory effort. Piston 706 and spring 708 can be placed at other positions in the airflow pathway of dry powder inhaler 100. During an inspiratory maneuver, airflow entering the air conduit 704 within housing 102 goes around piston 706, and moves piston 706 to compress spring 708. This airflow control mechanism during inhalation indicates inspiratory effort through a tactile sensation. In one embodiment, the mechanism indicates inspiratory effort through an audible click. In another embodiment, the mechanism indicates inspiratory effort through a tactile sensation and/or an audible click. Mouthpiece engaging section 122 of housing 102 has one or more protrusions such as mating structures 902 that mates with mouthpiece chamber 112 to secure mouthpiece when dry powder inhaler 100 is in use.

In operation, removable mouthpiece assembly 104 is rotated from a storage position to a cartridge loading/unloading position wherein lid 110 is opened and a cartridge containing medicament is placed into mouthpiece chamber 112 and securely seated. Lid 110 contains an anvil 1102 (FIG. 11) inside which, if a cartridge is inserted in the correct position, the anvil will further insure the cartridge achieves a proper vertical alignment. A downward push of lid 110 closes the cover and removable mouthpiece assembly 104 can rotate to the dosing position, wherein a registration securement holds removable mouthpiece assembly 104 in place. If the proper vertical alignment is not achieved lid 110 cannot be fully closed and subsequent removable mouthpiece assembly 104 rotation cannot occur. This provides an interlock mechanism.

FIG. 9 illustrates removable mouthpiece assembly 104 which has been separated from housing 102. Removable mouthpiece assembly 104 comprises mouthpiece chamber 112, lid 110 articulated to removable mouthpiece assembly 104 so that in a closed position lid 110 covers mouthpiece chamber 112, and mouthpiece oral placement section 106 having airflow conduit 714 with mouthpiece exit port 302. Mouthpiece chamber 112 comprises air inlet port 508, one or more flanges 506 having gaps and mating structure 902 for mating with and securing removable mouthpiece assembly 104 with housing 102. Flange 506 positioned at the bottom end of mouthpiece chamber 112 is provided which is structurally configured to engage with housing 102, and comprises multiple segments having gaps in between the segments; the gaps section contains mating structure 902 for mating with housing 102. The multiple segments of flange 506 and gaps between the segments can be position at predetermined positions of mouthpiece chamber 112 to effectuate proper securement of removable mouthpiece assembly 104 in housing 102.

Figure 10:
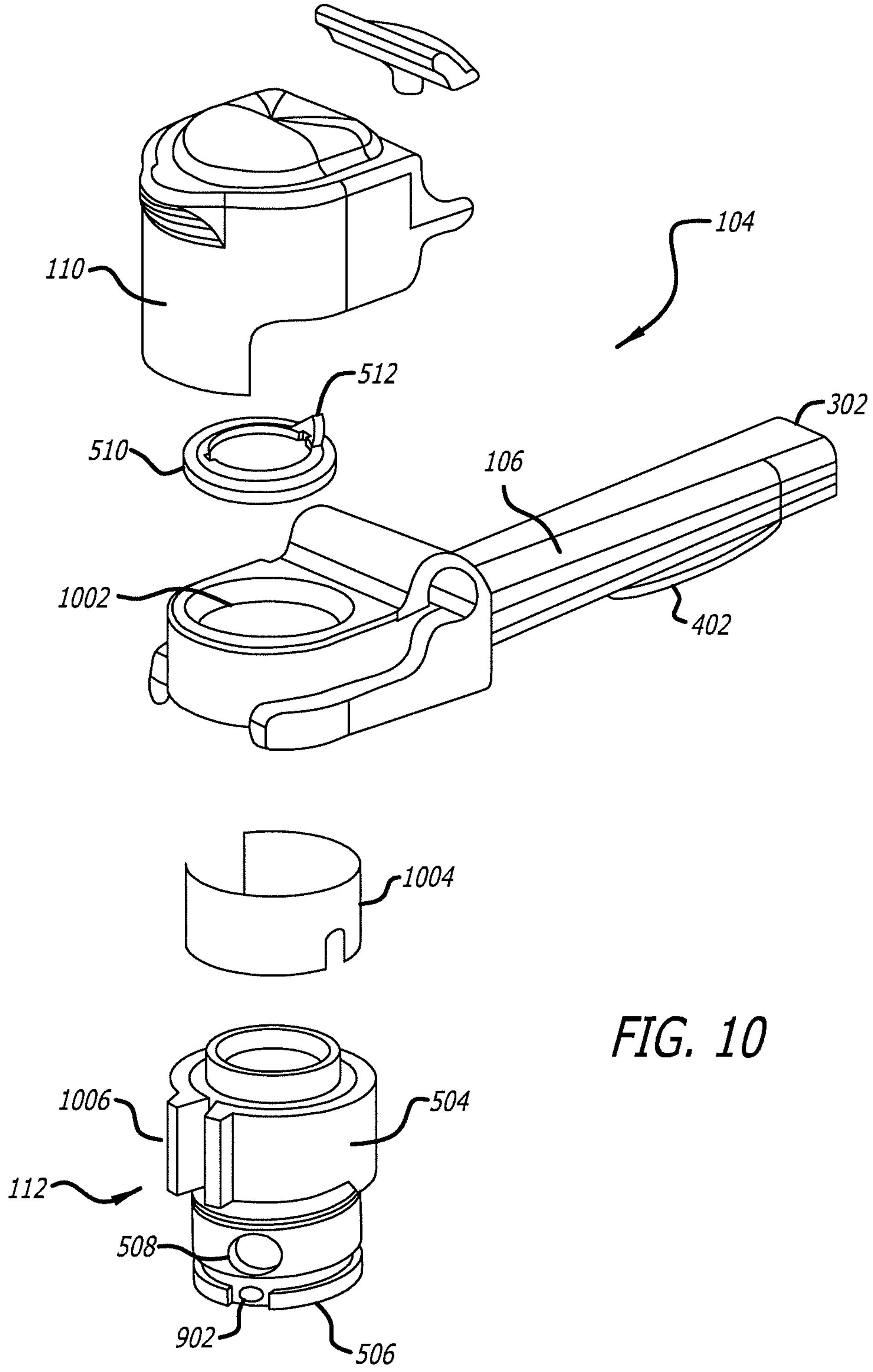
FIG. 10 illustrates the dry powder inhaler of FIG. 1, showing an exploded view of the mouthpiece subassembly.

FIG. 10 is an exploded view of removable mouthpiece assembly 104. Mouthpiece chamber 112 comprises drive key 510 with indicator 512, lid 110, mouthpiece oral placement section 106, cartridge securing mechanism 1002, a radial spring 1004, one or more belts 504 and interlock detents 1006.

In embodiments described herein, dry powder inhaler 100 is structurally configured to effectuate a tunable airflow resistance, which is modular. The resistance of dry powder inhaler 100 can be modified, by varying the cross-sectional area at any section of air conduit 704 of the inhaler. In one embodiment, dry powder inhaler 100 can have a airflow resistance value of from about 0.08 to about 0.13 square root of kPa/liters per minute.

Figure 11:
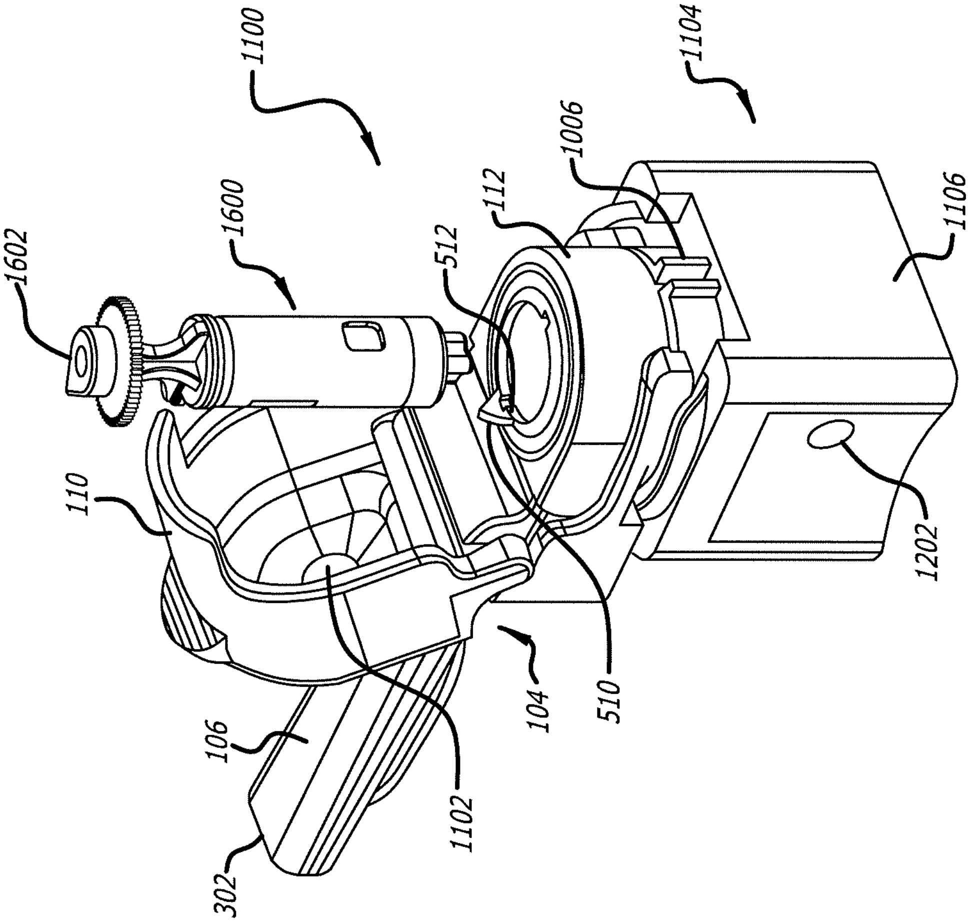
FIG. 11 illustrates an alternate embodiment of the dry powder inhaler system showing the inhaler in a cartridge loading position.

In an alternate embodiment illustrated in FIGS. 11-14, dry powder inhaler 100 comprises alternate housing 1104 configured to be compact and comprises a square-shape configuration which snuggly fits with removable mouthpiece assembly 104. Removable mouthpiece assembly 104 is similar in structure, if not identical in some embodiments, to the embodiment described with respect to FIGS. 1-10. FIG. 11 depicts alternate dry powder inhaler 1100 in the cartridge load/unload position with lid 110 open, mouthpiece oral placement section 106, mouthpiece exit port 302, anvil 1102, mouthpiece chamber 112 and interlocking mechanism 604 (FIG. 6). Cartridge 1600 has tear drop 1602 indicator for aligning to the indicator 512 of mouthpiece chamber 112 for proper insertion. Alternate housing 1104 in this embodiment, has an air inlet located in one of the side walls; however, in alternate embodiments the air inlet can be one or more holes placed in other positions, for example, in alternate housing back wall 1106. Alternate dry powder inhaler 1100 can have one or more openings in the housing of variable size or shape and locations.

Cartridges such as cartridge 1600 can be adapted to the dry powder inhaler containing a dry powder medicament for inhalation, and are configured to deliver a single unit dose of a medicament. In one embodiment, cartridge 1600 can be structurally configured to contain a dose of, for example, 0.5 mg to about 30 mg of dry powder for inhalation.

Figure 12:
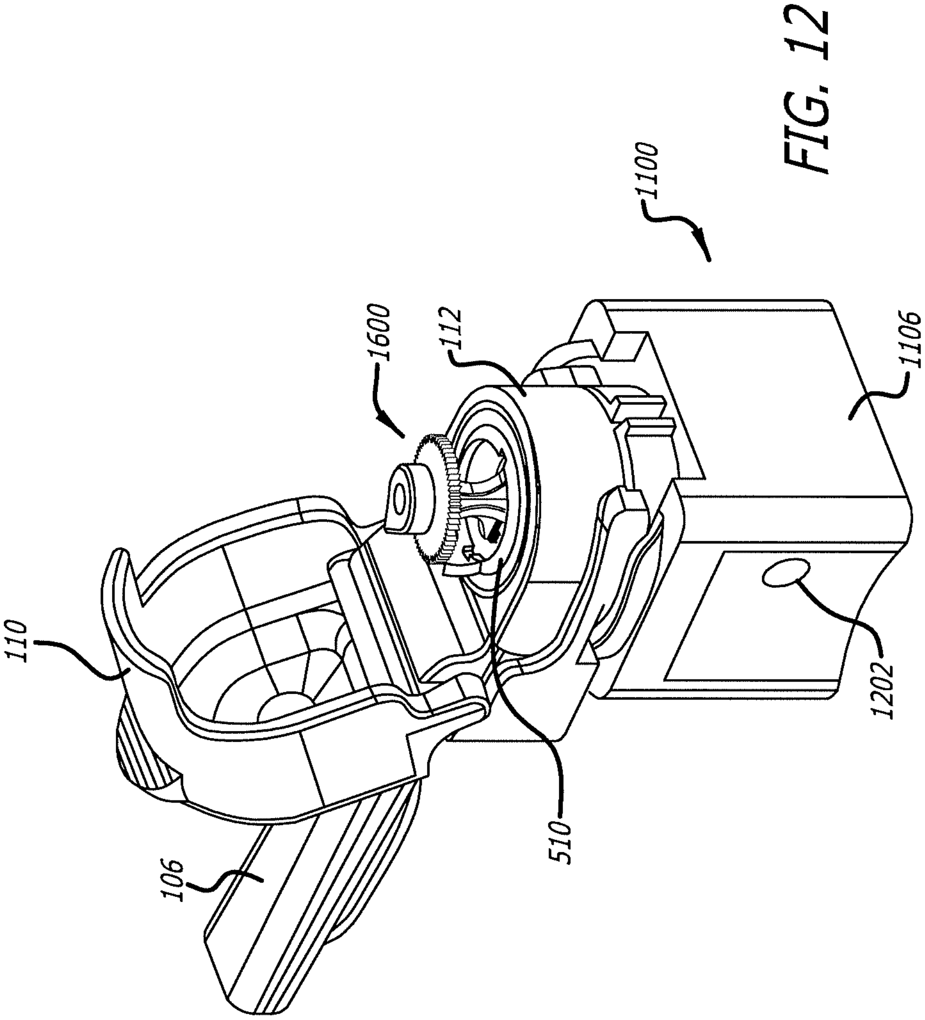
FIG. 12 illustrates the embodiment of FIG. 11 with a cartridge loaded into the dry powder inhaler with the cap open.
Figure 13:
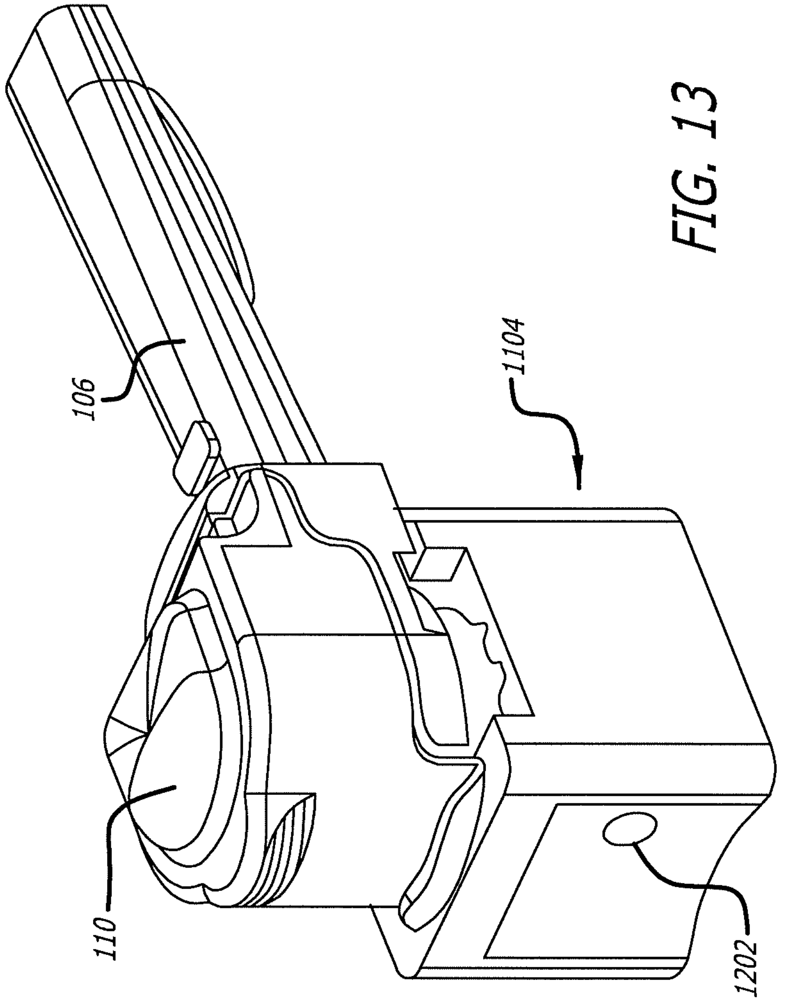
FIG. 13 illustrates the embodiment of FIG. 11 showing the dry powder inhaler in an inhalation position.

FIG. 12 illustrates an alternate dry powder inhaler 1100 with cartridge 1600 loaded and ready for closure of lid 110. As can be seen, lid 110 is in the open position, mouthpiece chamber 112 and alternate housing 1104 with alternate air inlet 1202. FIG. 13 depicts the dry powder inhaler system of FIG. 12 in the dosing position and ready for inhalation.

Figure 14:
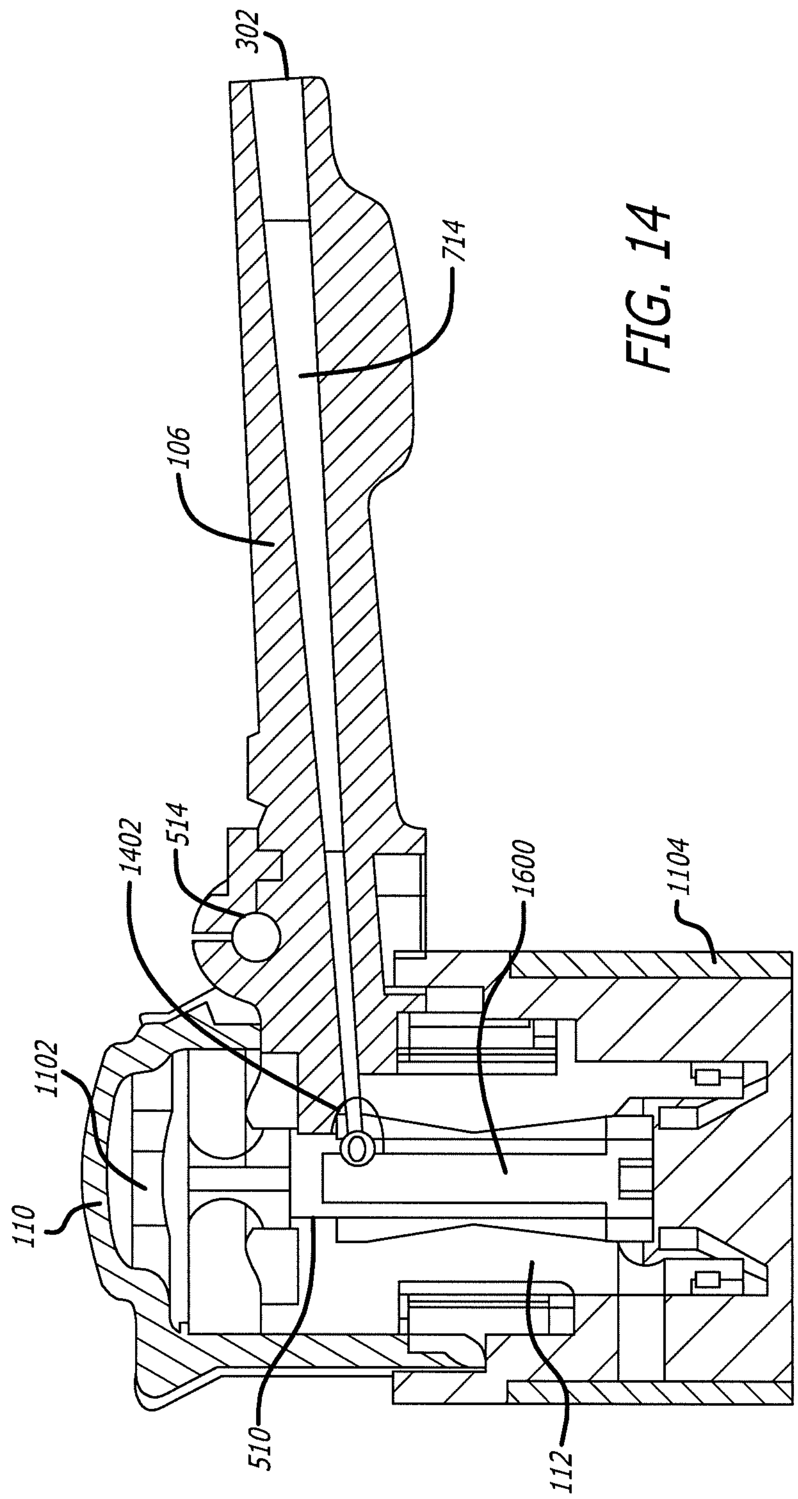
FIG. 14 illustrates the embodiment of FIG. 13 showing the dry powder inhaler in inhalation position as a cross-section through the mid-longitudinal axis.

FIG. 14 depicts a cross-section of alternate dry powder inhaler 1100 of FIG. 13, showing the internal features of the inhaler and cartridge system. Lid 110 securely holds cartridge 1600 by way of anvil 1102, which is then securely installed in mouthpiece chamber 112. The airflow conduit 714 of mouthpiece oral placement section 106 with mouthpiece inlet port 1402 and mouthpiece exit port 302.

Figure 15:
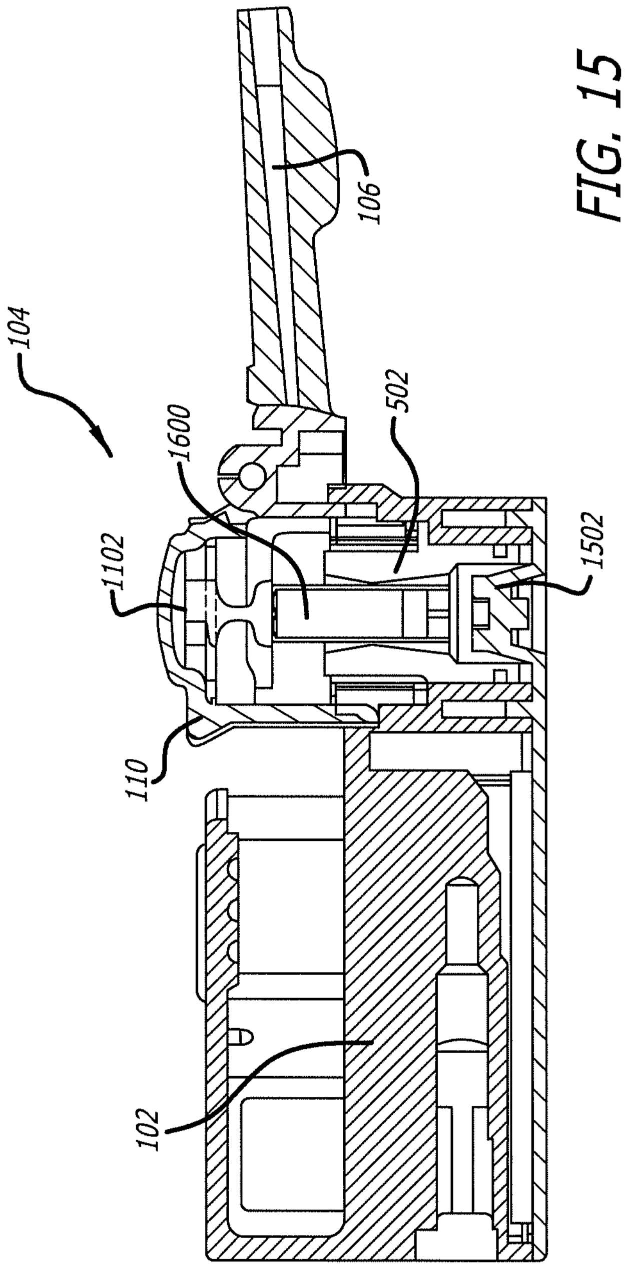
FIG. 15 illustrates a cross-section of an embodiment wherein the dry powder inhaler is shown in the dosing position and containing a cartridge.

In some embodiments, as shown in FIG. 15, dry powder inhaler 100 comprises a removable mouthpiece assembly 104 comprising lid 110 over cartridge holder area 502 movable from a closed to an open position, having anvil 1102 which engages with cartridge 1600 in a closed position, wherein the housing further comprises an air flow control mechanism comprising check valve 1502.

In embodiments described herein, the dry powder inhaler system in use has a predetermined airflow distribution around and through a cartridge operably configured to mix a medicament with air forming a powder plume for delivery to a patient's pulmonary system. Predetermined airflow distribution through the cartridge can range from about 10 to about 30% of total airflow volume entering the dry powder inhaler during inhalation. Predetermined airflow distribution around the cartridge can range from about 70 to about 90% of total airflow volume. Predetermined cartridge bypass airflow and exiting airflow through the cartridge converge to further shear and deagglomerate the powder medicament prior to exiting the mouthpiece outlet port.

Figure 16:
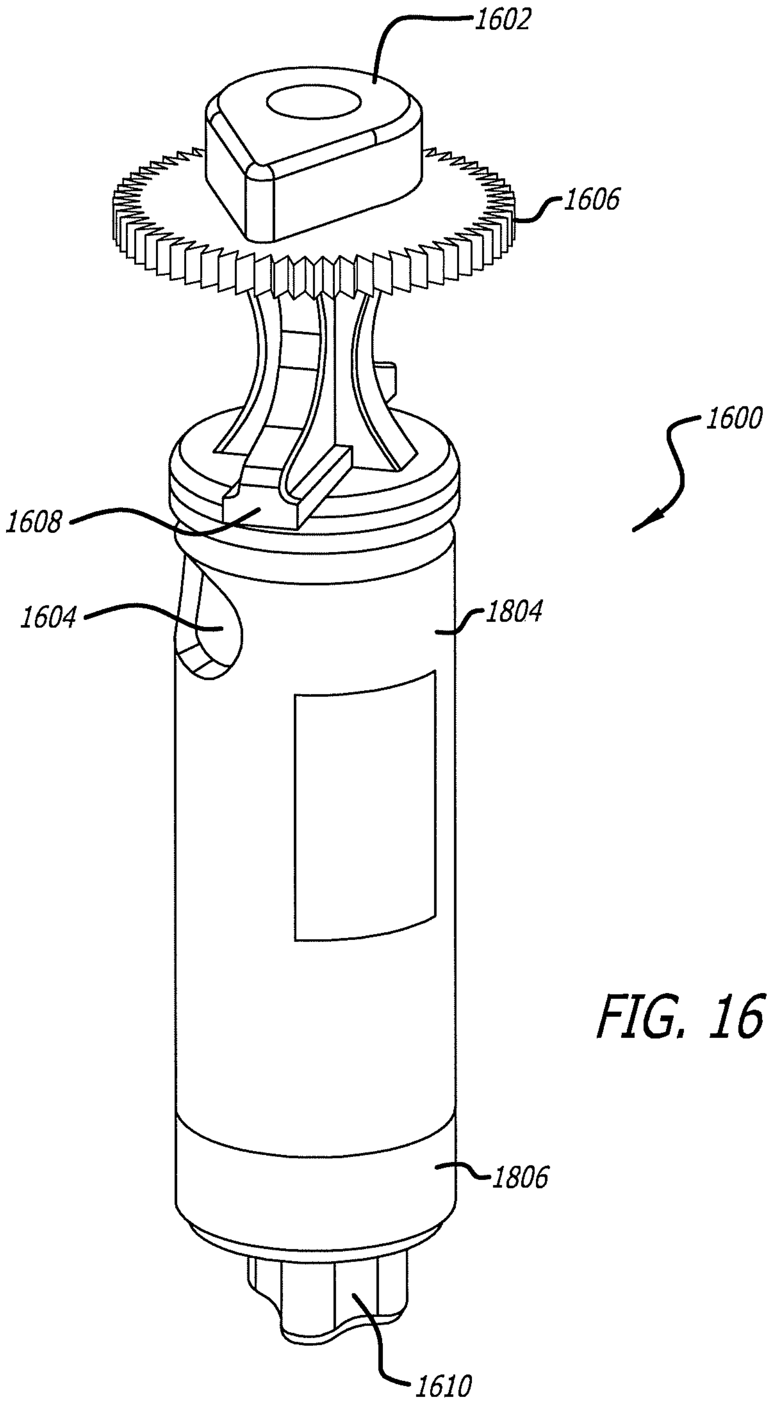
FIG. 16 illustrates an embodiment of a three dimensional side view of a cartridge for use with the dry powder inhalation system.
Figure 17:
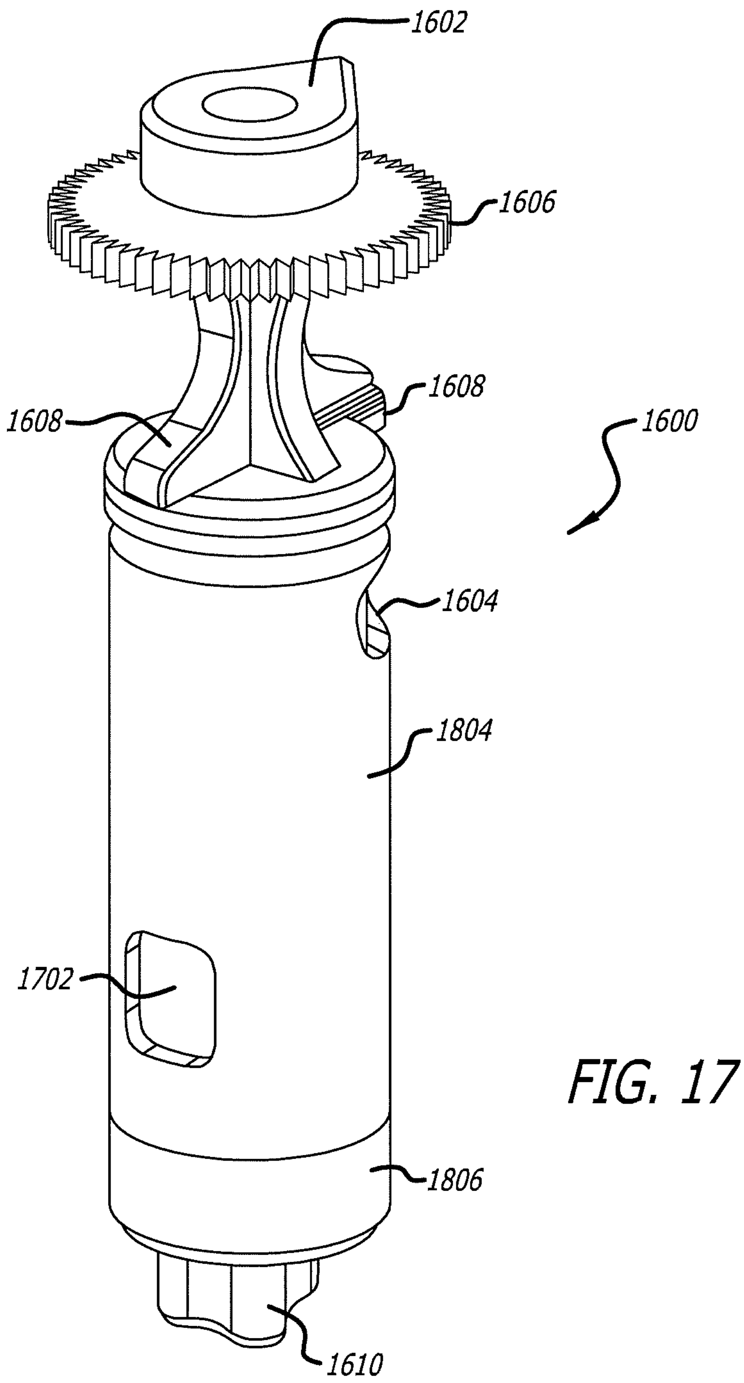
FIG. 17 illustrates an embodiment of a three dimensional back side view cartridge for use with the dry powder inhalation system.
Figure 18:
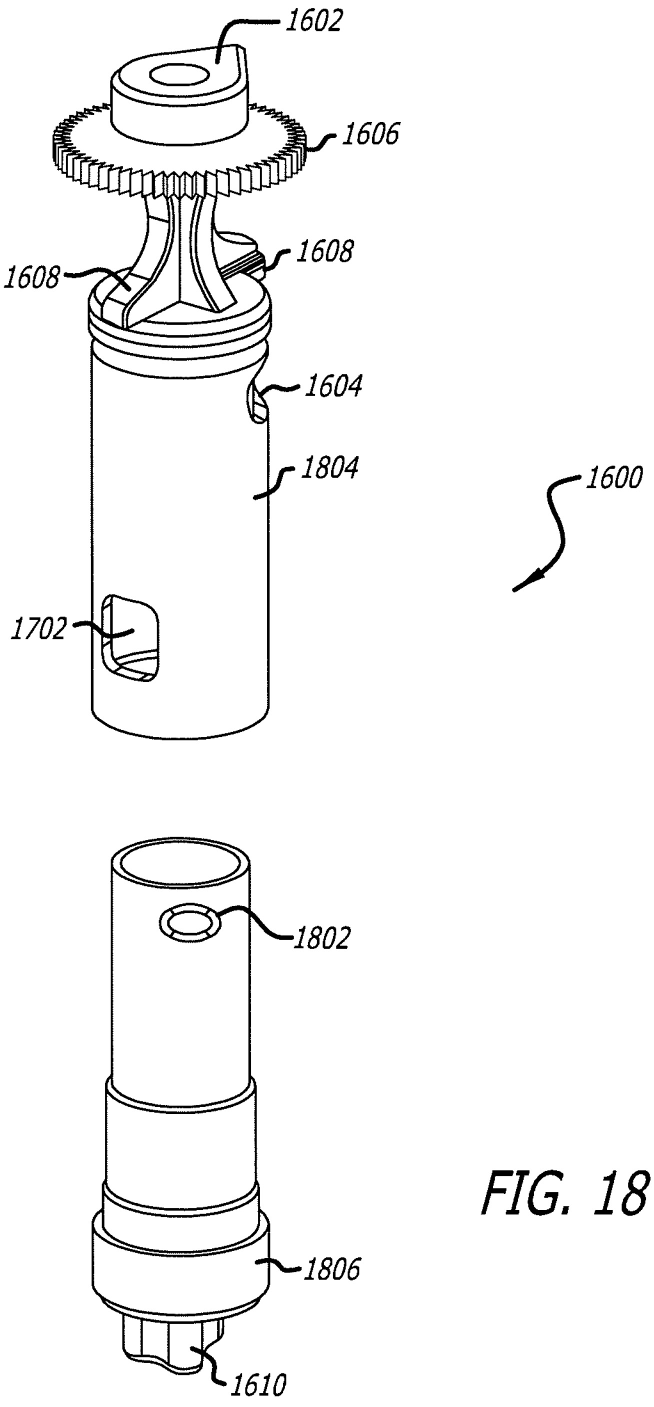
FIG. 18 illustrates an embodiment of an exploded three dimensional view of the cartridge for use with the dry powder inhalation system.

In one embodiment, the medicament containing cartridge 1600 as shown in FIGS. 16-18 can comprise a structure with a defined shape having a wall with one or more first apertures 1604, second aperture 1702 and third aperture 1802, tear drop 1602, grasping feature 1606, and first inhaler keying mechanism 1608 and second inhaler keying mechanism 1610. Cartridge 1600 has a closed configuration moveable to an open configuration for dosing a powder medicament or from an open to a closed position after use. Cartridge 1600 further comprises an outer surface and an inner surface defining an internal volume; wherein the closed configuration restricts communication, such as air transit to or through the internal volume, and the open configuration forms an air passage through the internal volume to allow a powder medicament contained therein to be aerosolized and delivered to a patient in an airflow stream created by the user. The open configuration is established by providing one or more apertures (e.g. first aperture 1604, second aperture 1702 and third aperture 1802), holes, slits or windows in the cartridge walls that can have beveled edges to direct airflow. In one embodiment, cartridge 1600 can be configured of two elemental parts, for example, two segments (e.g. first segment 1804 and second segment 1806) that can have apertures in their walls that can align with one another in the open configuration and in opposing positions where the apertures at not in alignment. In one embodiment, for example, cartridge 1600 can be structurally configured as two separate elements which can fit into one another and be moveable about one another; each having openings which can align with one another, similarly as the capsules described in U.S. Pat. No. 7,305,986, which is fully incorporated herein by reference as if part of this specification. In this embodiment, however, cartridge 1600 is designed to integrally function with the dry powder inhaler and can be moved within the inhaler to predetermined positions In one embodiment, a method of delivering an active ingredient comprising: a) providing a dry powder inhaler comprising, a housing and a mouthpiece, the mouthpiece comprising a chamber containing a cartridge with a dry powder formulation comprising a diketopiperazine and the active agent; the inhaler having a flow distribution of about 10% to 30% of the airflow going through the cartridge, and b) delivering the active ingredient to an individual in need of treatment by inhaling deep and rapidly for about 4 to 6 seconds and optionally repeating step b).

In embodiments described herein, the dry powder inhaler can deliver a dose of a dry powder formulation to a patient at pressure differentials between 2 and 20 kPa.

In still yet a further embodiment, the method of treating hyperglycemia and/or diabetes comprises the administration of an inhalable dry powder composition comprising a diketopiperazine having the formula 2,5-diketo-3,6-di(4-X-aminobutyl)piperazine, wherein X is selected from the group consisting of succinyl, glutaryl, maleyl, and fumaryl. In this embodiment, the dry powder composition can comprise a diketopiperazine salt. In still yet another embodiment of the present invention, there is provided a dry powder composition, wherein the diketopiperazine is 2,5-diketo-3,6-di-(4-fumaryl-aminobutyl)piperazine (FDKP), having the structure:

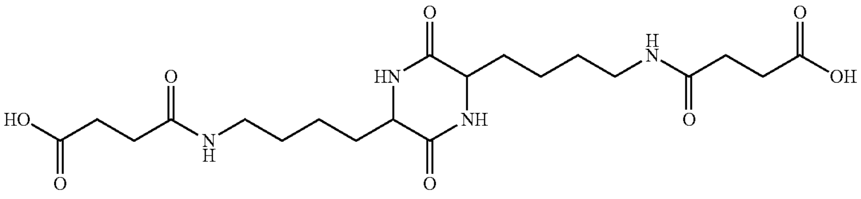

FDKP with or without a pharmaceutically acceptable carrier, or excipient.

In one embodiment, the inhalation system comprises a breath-activated dry powder inhaler, a cartridge containing medicament, wherein the medicament can comprise a diketopiperazine and an active agent. In some embodiments, the active agent comprises peptides and proteins. In another embodiment, the inhalation system comprises a cartridge containing medicament wherein the peptide or protein can be an endocrine hormone, including, insulin, GLP-1, calcitonin, parathyroid hormone, parathyroid hormone related protein (PTHrP), and analogs thereof and the like.

In another embodiment, the dry powder medicament may comprise a diketopiperazine and a pharmaceutically active ingredient. In this embodiment, the pharmaceutically active ingredient can be any type. In certain embodiments, the active ingredient comprises a peptide, a protein, a hormone, analogs thereof or combinations thereof, wherein the active ingredient is insulin, parathyroid hormone 1-34, glucagon-like peptide-1 (GLP-1), oxyntomodulin, peptide YY, interleukin 2-inducible tyrosine kinase, Bruton's tyrosine kinase (BTK), inositol-requiring kinase 1 (IRE1), heparin, or analogs thereof. In a particular embodiment, the pharmaceutical composition comprises fumaryl diketoperazine and insulin.

In a particular embodiment, the dry powder inhalation system can comprise a cartridge including a formulation for pulmonary delivery comprising FDKP and a peptide including, for example, insulin or GLP-1, which can be provided for use in different dosage strength in a single or multiple cartridges. In one embodiment, the system can deliver the dosage efficiently, with consistency and in a linear manner. In this embodiment, for example, multiple cartridges of a single dose to be administered to a subject can be interchangeably replaced or substituted by a providing the system with a single cartridge having the sum of the dosage strength of the multiple cartridges. In further embodiment, the system can deliver a proportional, bioequivalent dose with a single cartridge. In an exemplary embodiment using the system for treating diabetes with inhalable insulin powders, the system can use two 15 U cartridges of an inhalation powder comprising insulin and FDKP or the system can use one 30 U single cartridge containing an inhalation powder comprising FDKP and deliver bioequivalent doses of insulin to a patient. Similarly, the system can be used to deliver higher doses, for example, three 15 U cartridges of an inhalation powder comprising insulin and FDKP can be used, or one 15 U cartridge plus one 30 U cartridge, or a single 45 U cartridge containing the inhalable insulin and FDKP formulation; or four 15 U cartridges of an insulin and FDKP formulation can be interchangeable with one 60 U cartridge of insulin and FDKP formulation. Alternatively, two 30 U cartridges containing an inhalable insulin and FDKP formulation can be interchanged for one 60 U cartridge of the insulin and FDKP formulation.

In the embodiments described herein, the dry powder inhalation system accomplishes insulin exposure proportional to a dosage so that the dosages are interchangeable. In an embodiment, the dosage can be provided as filled dose.

EXAMPLES

The following examples are included to demonstrate certain embodiments of the invention. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention.

Example 1

Dosage Strength Interchangeability

The study was conducted in subjects with type 1 diabetes mellitus. This study was conducted to determine if a formulation for pulmonary delivery comprising insulin and a diketopiperazine in the formulation, 1) could be delivered consistently using different dosage strengths and 2) if linearity of dosing could be achieved with proportional doses, given that interchangeability of dosage strengths can be important for patient safety. A prior art marketed inhaled insulin did not achieve this and dose combinations were nonequivalent leading to a potential risk of incorrect dosing. Therefore, an important goal in the development of the pulmonary delivery system with a formulation comprising insulin and FDKP (insulin-FDKP) was to achieve dose linearity across the therapeutic dose range.

In the study, comparisons of insulin exposure following inhalation of two 15 U cartridges of an insulin inhalation powder to one 30 U cartridge of insulin inhalation powder were made. In addition, insulin bioavailability from a 30 U cartridge of insulin-FDKP inhalation powder was calculated, compared to a 10-IU subcutaneous (sc) injection of insulin lispro (rapid acting analogue [RAA]).

A phase I, open-label, single-dose, repeat administration study in subjects with type 1 diabetes (T1DM) was conducted to assess the pharmacokinetic profile or PK of 30 U of insulin-FDKP dosed as a single 30 U cartridge and compared to two 15 U cartridges administered with the present inhalation system. A 10 U subcutaneous injection of the rapid acting insulin analogue (RAA, HUMALOG® (Eli Lilly and Company, Indianapolis, IN)) was also tested. Subjects (age: 19-61 yrs) were randomized to 1 of 6 sequences. Fasted subjects received insulin-FDKP or RAA 4 to 6 hrs after initiating a hyperinsulinemic-euglycemic clamp. Randomization determined the order of insulin-FDKP dosing (first 2 treatment (tx) visits), and the location of the RAA injection (abdomen, arm or leg; $3^{rd}$ tx visit). After dosing blood samples were taken and analyzed for insulin, insulin lispro and fumaryl diketopiperazine (FDKP (insulin-FDKP tx only)). When studying insulin-FDKP, the basal insulin infusion was performed with HUMALOG®, and when studying HUMALOG®, regular human insulin was used. The analytical methodologies enabled the independent measurement of each insulin tested.

Table 1 shows the results from the study. The mean insulin exposures ($AUC_{0-360}$) of a single 30 U cartridge or two 15 U cartridges were comparable. FDKP mean exposure ($AUC_{inf}$) was also similar. Insulin and FDKP exposure, $t_{max}$ and $t_{1/2}$ (FDKP) were the same regardless of the number of cartridges. Due to the significantly different PK profiles of insulin-FDKP and RAA, the mean relative exposure (AUC) ratio is dependent upon the time interval studied. The mean relative insulin exposure (insulin-FDKP: HUMALOG® AUC, dose normalized geometric means) when assessed at time intervals of 0-180 min and 0-360 min was 24% to 18%.

TABLE 1

| | 2 × 15 U TI cartridges | 1 × 30 U TI cartridge | 10 IU Humalog |
|---|---|---|---|
| Insulin PK parameters | | | |
| $AUC_{0-360}$ (μU*min/mL) | 3337 | 3397 | 5915 |
| $AUC_{0-180}$ (μU*min/mL) | 3121 | 3199 | 4432 |
| $C_{max}$ (μU/mL) | 65.72 | 69.08 | 42.60 |
| $t_{max}$ (min) | 10 | 10 | 60 |
| 90% CI (Geometric Mean Ratio:$AUC_{0-360}$) | 0.846, 1.141 | | ND |
| FDKP PK parameters | | | |
| $AUC_{0-480}$ (ng*min/mL) | 19552 | 20159 | — |
| $AUC_{0-inf}$ (ng*min/mL) | 23146 | 24355 | — |
| $C_{max}$ (ng/mL) | 118 | 131 | — |
| $t_{max}$ (min) | 6 | 5 | — |
| 90% CI(Geometric Mean Ratio:$AUC_{0-480}$) | 0.867, 1.084 | | — |

Figure 19:
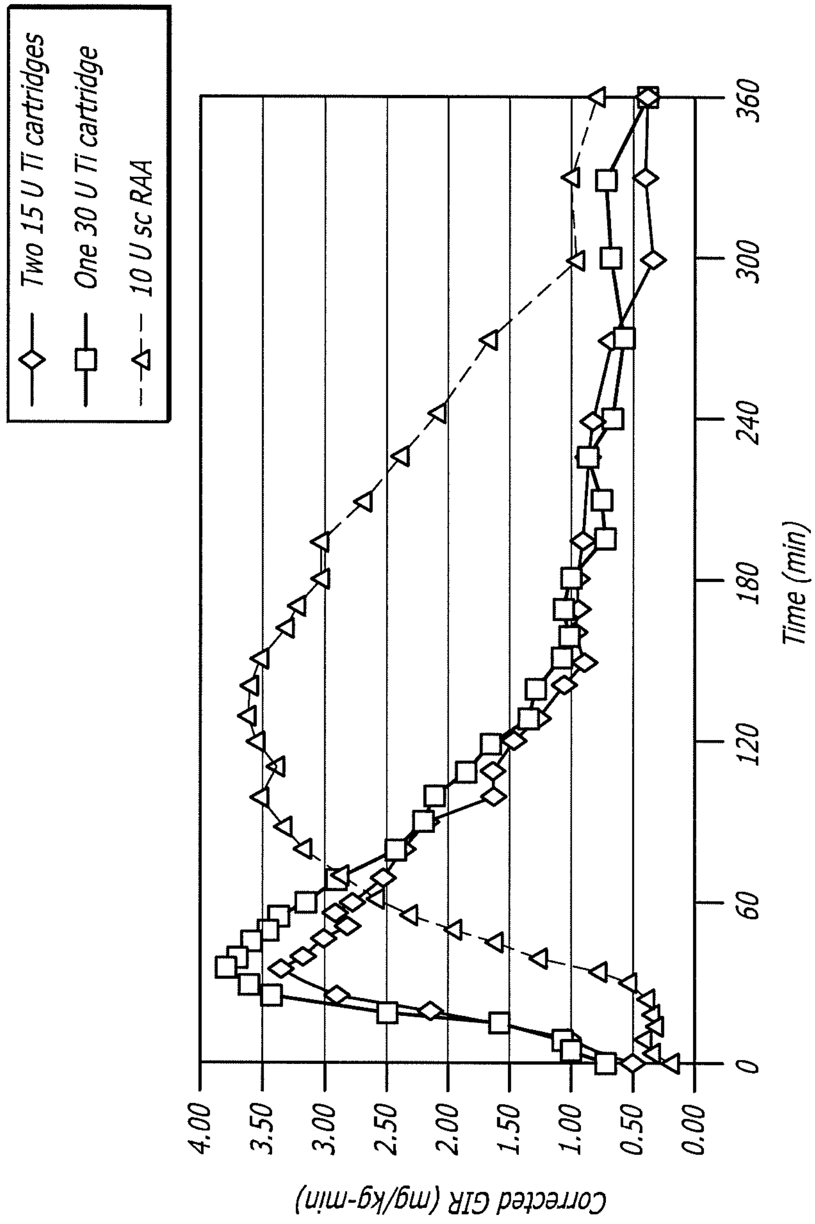
FIG. 19 illustrates a mean baseline-corrected GIR (glucose infusion rate) for two 15 U cartridges and one 30 U cartridge of an inhalation powder comprising insulin and fumaryl diketopiperazine, and for 10 IU of RAA.

This study also evaluated the effects of the dosages administered and the glucose infusion rate (GIR) requirements of the patients in the study. FIG. 19 illustrates the results of the GIR evaluation. The data show the mean baseline-corrected glucose infusion rate (GIR) for two 15 U cartridges and one 30 U cartridge of insulin-FDKP inhalation powder and for the 10 IU of RAA. GIRs after both treatments of insulin-FDKP inhalation powders reached a maximum level by approximately 30 minutes after administration, whereas GIR peaked approximately 150 minutes after administration of sc RAA. The GIRs for insulin-FDKP inhalation powder returned toward baseline by approximately 180 minutes versus 300 minutes for RAA. In conclusion, the glucose-lowering effect of insulin-FDKP inhalation powder of both dosage forms tested was comparable based on GIR AUC, $GIR_{max}$, and $GIRt_{max}$.

Example 2

Dry Powder Inhaler Resistance Value Measurements

Figure 20A:
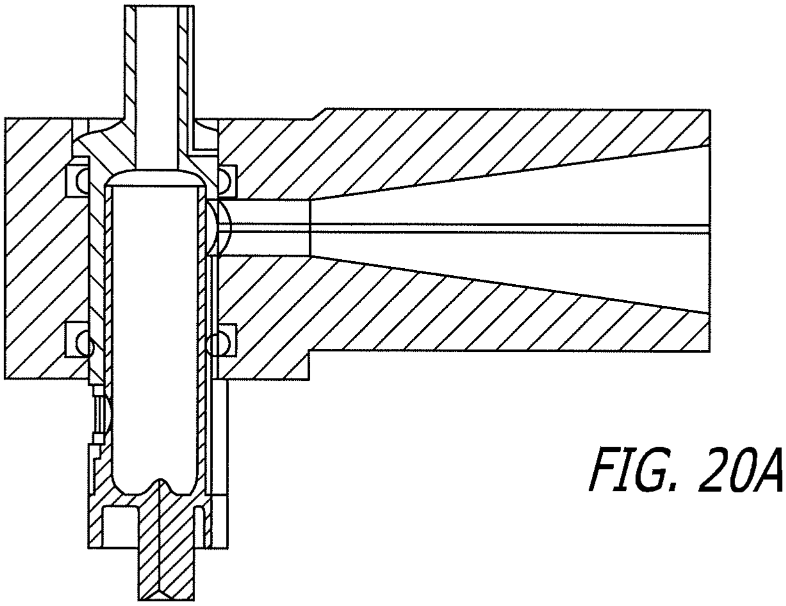
FIG. 20A depicts a schematic representation of a cartridge loaded into a cartridge rig in cross-section for measuring pressure across the cartridge.
Figure 20B:
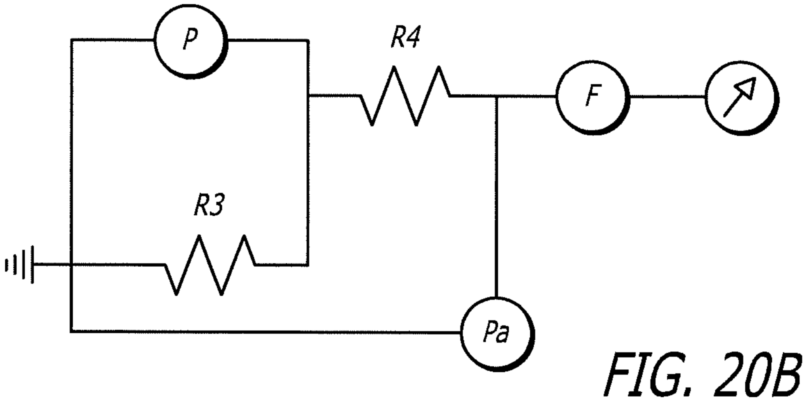
FIG. 20B illustrates a diagram of a resistance circuit illustrating the various resistors associated with the cartridge rig illustrated in FIG. 20A.
Figure 21A:
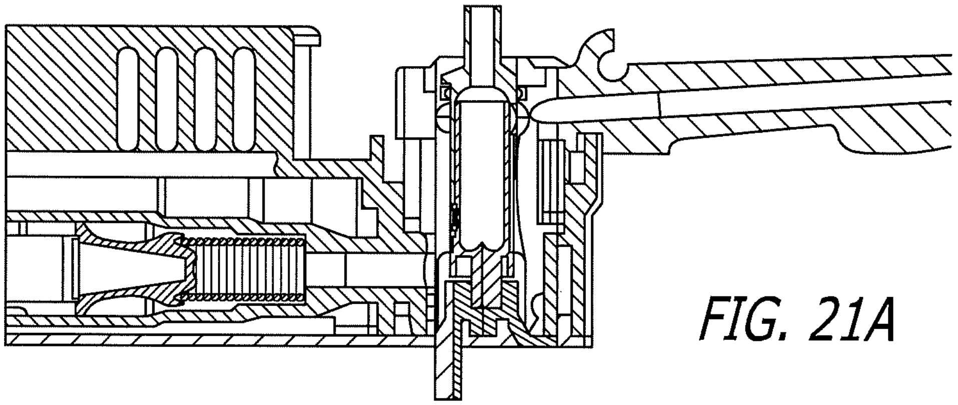
FIG. 21A illustrates a schematic representation of a portion of the inhaler in cross-section showing components parts.
Figure 21B:
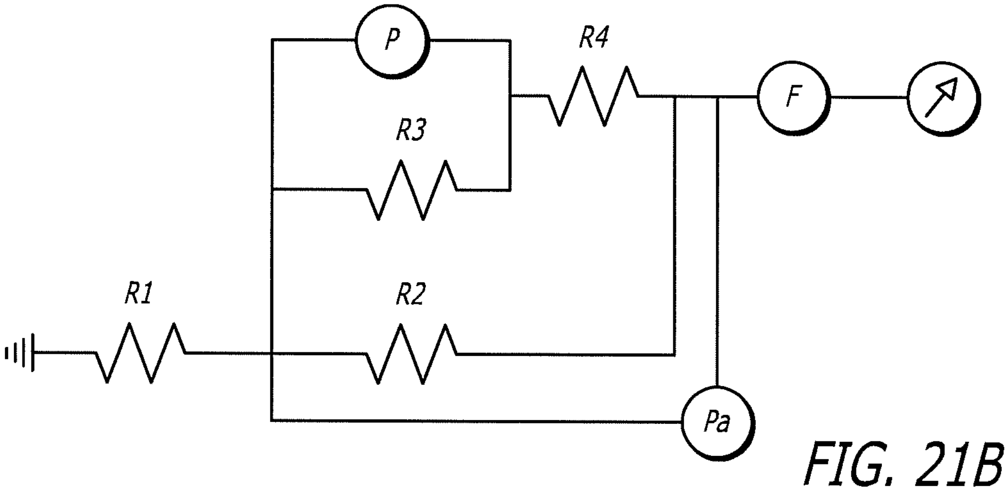
FIG. 21B illustrates a diagram of a resistance circuit of an inhaler embodiment of FIG. 21A used for measuring the resistance and pressure of the device.

The total inhaler and cartridge resistance can be measured due to inlet and outlet ports of a cartridge acting as resistors in series. First, the resistance due to the inlet port is measured in the cartridge rig. The representation of a circuit diagram form for the cartridge rig is illustrated in FIGS. 20A and 20B, wherein the cartridge sits in the holder in an open configuration and the circuitry is defined such that R3 represents the resistance to airflow into the cartridge; R4 represents the resistance to airflow leaving the cartridge; Pa is the pressure differential across the cartridge and P represents the pressure measured across the inlet and outlet ports. Secondly, the resistance due to the inhaler system comprising the inhaler and cartridge is determined as illustrated in FIGS. 21A and 21B, wherein R1 represents the resistance due to the float or valve; R2 represents the resistance to air flow around the cartridge; R3 represents the resistance to airflow through the cartridge; R4 represents the resistance to airflow leaving the cartridge; P represents the measured pressure; Pa represents the pressure across the system and F represents the total flow measurement. Once values are determined for the resistors and having pressure drop measurements, the flow balance distribution through and around the cartridge can be determined.

Measurements were made of the cartridge and cartridge/inhaler system dosing configuration and the resistance to airflow through the cartridge, R3 was determined from the formula:

$$R3 = \frac{\sqrt{P}}{F}$$

Based on the measurements made as illustrated in FIGS. 20A-21B, the resistance due to the inlet and outlet ports were determined and the values used to calculate the flow balance of the system in particular the flow balance through the cartridge using the formula above, which is determined as the √P divided by R3. The flow balance distribution through the cartridge for the present inhaler and cartridge system was calculated to be in the range from about 10% to about 30% with an average of approximately 15.92%.

Figure 22:
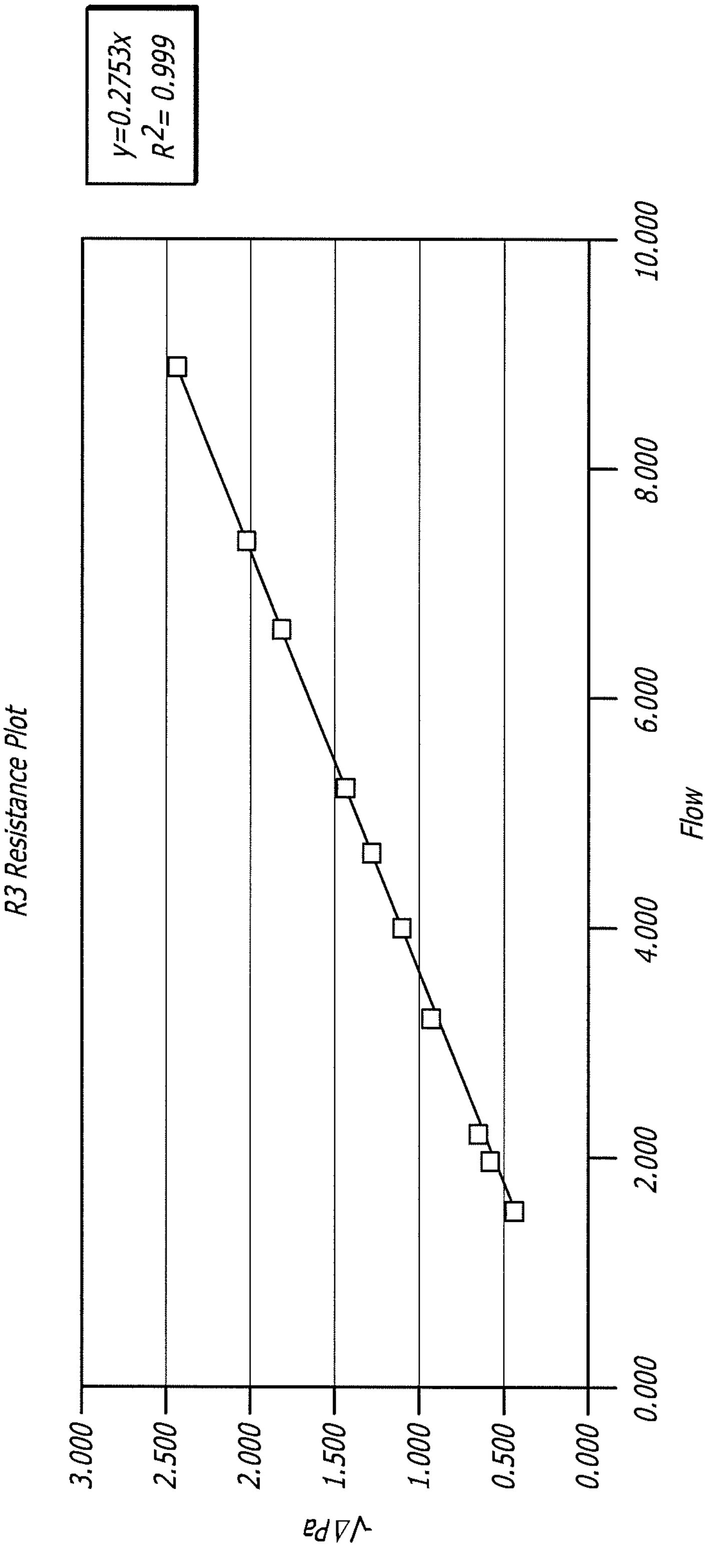
FIG. 22 depicts a linear regression plot illustrating the resistance measured through an exemplary cartridge rig tested or R3, at flow rates between 2 and 9 liters/min.

The resistance for the inhaler cartridge system tested herewith can be determined experimentally from the values obtained in the same manner. The resistance for the present inhalers when calculated from the measurements resulted in airflow resistance values of between 0.08 and 0.15 √kPa/liters per minute. FIG. 22 depicts a linear regression plot illustrating the resistance measured through an exemplary cartridge rig tested or R3, at flow rates between 2 and 9 liters/min. As shown in FIG. 22, the resistance through the cartridge ($R^2$) tested was determined as equaling to 0.999 √kPa/liters per minute.

Therefore, the inhalers can be structurally configured to have tunable airflow resistance by varying the cross-sectional area at any section of the airflow pathway of the inhaler and cartridge system.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of treating hyperglycemia, the method comprising:

administering an inhalable dry powder composition comprising a diketopiperazine having the formula 2,5-diketo-3,6-di(4-X-aminobutyl)piperazine, wherein X is selected from the group consisting of succinyl, glutaryl, maleyl, and fumaryl, via an inhalation system for pulmonary delivery, said inhalation system comprising a housing and a mouthpiece, said housing including an inlet and an outlet port, and said mouthpiece configured to move translationally within said housing; and wherein the inhalation system is configured to be separable into two principal component parts, and wherein said inhalation system provides an airflow resistance ranging from 0.08 and 0.15 ΠkPa/liters per minute.

2. The method of claim 1, wherein the inhalable dry powder composition further comprises an active agent.

3. The method of claim 2, wherein the active agent comprises a peptide and/or a protein.

4. The method of claim 3, wherein the peptide or protein is an endocrine hormone, insulin, GLP-1, calcitonin, a parathyroid hormone, a parathyroid hormone related protein (PTHrP), or an analog thereof.

5. The method of claim 1, wherein the inhalation system for pulmonary delivery comprises:

a dry powder inhaler comprising a housing and a mouthpiece, said housing including an inlet and an outlet port, and said mouthpiece configured to move translationally within said housing;

a cartridge adapted to said dry powder inhaler and containing a dry powder medicament for inhalation;

said dry powder inhaler system comprising air conduits configured to provide a predetermined airflow distribution around and through said cartridge operably configured to mix the medicament with air forming a powder plume for delivery to a patient's pulmonary system; wherein said predetermined airflow distribution through said cartridge ranges from about 10 to 30% of total airflow volume entering said dry powder inhaler during inhalation.

6. The method of claim 5, wherein the predetermined airflow distribution around said cartridge ranges from about 70 to 90% of total airflow volume.

7. The method of claim 5, wherein said housing having a top wall, a bottom wall, a first side wall and a second side wall; and a mouthpiece engaging section, a mouthpiece storage section, and an air intake section having a conduit with a first opening corresponding to the inlet to allow ambient air intake and a second opening corresponding to the inlet in communication with the mouthpiece engaging section which allows air flow therethrough;

said mouthpiece being separable from said housing and comprising a chamber structurally configured to house said cartridge and to engage with said mouthpiece engaging section of said housing; an oral placement section extending from said chamber and having an air inlet which communicates with said chamber and an air outlet in communication with ambient air.

8. The method of claim 7, wherein said mouthpiece engaging section of said housing has an outer wall, an inner wall and a bottom wall contiguous with the said first side wall, said second side wall and bottom walls respective of said housing, and configured to adapt to said mouthpiece chamber of said mouthpiece.

9. The method of claim 7, wherein said mouthpiece engaging section further comprises a protrusion from said bottom wall configured to receive and hold the medicament containing cartridge.

10. The method of claim 7, wherein the mouthpiece engaging section further comprises a securing mechanism from said inner wall structurally configured to engage said mouthpiece chamber of said mouthpiece.

11. The method of claim 7, wherein the mouthpiece chamber further comprises a flange having gaps which mate protrusions or projections from the inner wall of the mouthpiece engaging section.

12. The method of claim 7, wherein said mouthpiece is moveable from a storage position to a cartridge loading position to an inhalation position, and comprises a mixing chamber configured to hold the medicament containing cartridge and to have an opening which aligns with the second opening of the intake section in said inhalation position.

13. The method of claim 7, wherein the mouthpiece chamber comprises an air inlet and is configured to secure the medicament containing cartridge, and has an indicator to allow proper cartridge placement in the inhaler.

14. The method of claim 7, wherein the mouthpiece comprises a cap over the chamber, movable from a closed to open position, having an anvil which engages with the cartridge in a closed position.

15. The method of claim 7, wherein the housing further comprises an air flow control mechanism comprising a check valve.

16. The method of claim 7, wherein said dry powder inhaler system in use has the predetermined air flow distribution around and through said cartridge of air flow volume entering said chamber.

17. The inhalation system of claim 16, wherein the predetermined air flow distribution through said cartridge ranges from about 10% to 30% of the air flow volume entering the mixing section and from about 70% to about 90% of the air flow volume entering the mouthpiece chamber.

* * * * *